US012295362B2

United States Patent
Medi et al.

(10) Patent No.: US 12,295,362 B2
(45) Date of Patent: May 13, 2025

(54) FORMULATIONS AND PROCESSES FOR CAR T CELL DRUG PRODUCTS

(71) Applicant: Allogene Therapeutics, Inc., South San Francisco, CA (US)

(72) Inventors: Muneeswara Babu Medi, Chalfont, PA (US); Zhuojin Xu, San Francisco, CA (US); Jung S. Lee, South San Francisco, CA (US); Yajin Ni, San Diego, CA (US); Mark W. Leonard, Burlingame, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 129 days.

(21) Appl. No.: 17/592,105

(22) Filed: Feb. 3, 2022

(65) Prior Publication Data

US 2022/0241329 A1    Aug. 4, 2022

Related U.S. Application Data

(60) Provisional application No. 63/145,235, filed on Feb. 3, 2021.

(51) Int. Cl.
| | | |
|---|---|---|
| *A01N 1/125* | (2025.01) | |
| *A61K 40/11* | (2025.01) | |
| *A61K 40/31* | (2025.01) | |
| *A61K 40/42* | (2025.01) | |
| *C12N 5/0783* | (2010.01) | |

(52) U.S. Cl.
CPC .............. *A01N 1/125* (2025.01); *A61K 40/11* (2025.01); *A61K 40/31* (2025.01); *A61K 40/4211* (2025.01); *C12N 5/0636* (2013.01)

(58) Field of Classification Search
CPC ............ A61K 35/17; A61K 2039/5156; A61K 2039/5158; A61K 39/001112; A01N 1/0221; A01N 1/0242; A01N 1/0284; C12N 5/0636; C12N 2510/00; C07K 2317/622; C07K 2319/03; C07K 2319/33; C07K 14/7051; C07K 16/2803
See application file for complete search history.

(56) References Cited

U.S. PATENT DOCUMENTS

| | | |
|---|---|---|
| 4,816,567 A | 3/1989 | Cabilly et al. |
| 5,821,337 A | 10/1998 | Carter et al. |
| 6,319,494 B1 | 11/2001 | Capon et al. |
| 6,982,321 B2 | 1/2006 | Winter et al. |
| 7,087,409 B2 | 8/2006 | Barbas et al. |
| 7,527,791 B2 | 5/2009 | Adams et al. |
| 7,741,465 B1 | 6/2010 | Eshhar et al. |
| 2016/0066566 A1 | 3/2016 | Chang et al. |

FOREIGN PATENT DOCUMENTS

| | | |
|---|---|---|
| CN | 108552160 A | 9/2018 |
| WO | 2013153391 A1 | 10/2013 |
| WO | 2015120096 A2 | 8/2015 |

OTHER PUBLICATIONS

Gibco. Recovery Cell Culture Freezing Media, Product Manual. 2014. Publication No. MAN0007322. Downloaded on Oct. 10, 2023 from: https://assets.fishersci.com/TFS-Assets/LSG/manuals/12648010_cell_culture_freeze_media_Pl.pdf (Year: 2014).*
Ou et al. Novel biomanufacturing platform for large-scale and high-quality human T cells production. J Biol Eng. 2019; 13:34. (Year: 2019).*
Kielberg et al. Cryopreservation of Mammalian Cells—Protocols. 2010. Thermo Fisher, Publication No. TILSPNUNCTN14 0410. Downloaded on Oct. 11, 2023 from: https://assets.fishersci.com/TFS-Assets/LSG/Application-Notes/D19575.pdf (Year: 2010).*
English translation of CN108552160A Zhang et al. CAR-T cell cryopreservation liquid for direct venous retransfusion and preparation method and application of CAR-T cell cryopreservation liquid. 2018. Generated by Espacenet; no date for translation available.*
Almagro , et al., "Humanization of antibodies", Frontiers in Bioscience, vol. 13, pp. 1619-1633, (2008).
Dall'Acqua, William F., et al., "Antibody humanization by framework shuffling", Methods; 2005 36(1):43-60; DOI; 10.1016/j.ymeth.2005.01.005.
EPO , "Internal Search Report & Written Opinion", mailed on Aug. 5, 2020 for PCT/US2020/020042.
Finney, Helen , et al., "Chimeric Receptors Providing Both Primary and Costimulatory Signaling in T Cells from a Single Gene Product", J Immunol Sep. 15, 1998, 161 (6) 2791-2797.
Gross, Gideon , et al., "Therapeutic Potential of T Cell Chimeric Antigen Receptors (CARs) in Cancer Treatment: Counteracting Off-Tumor Toxicities for Safe Car T Cell Therapy", Annual Review of Pharmacology and Toxicology; vol. 56:59-83 (Volume publication date Jan. 2016) https://doi.org/10.1146/annurev-pharmtox-010814-124844.
Zadyar, Fariborz , et al.; Development of a Cryopreservation Protocol for Type A Spermatogonia; Journal of Andrology, vol. 23, No. 4, Jul./Aug. 2002.
Kalos, Michael , et al., "T Cells with Chimeric Antigen Receptors Have Potent Antitumor Effects and Can Establish Memory in Patients with Advanced Leukemia", Science Transnational Medicine, vol. 3 Issue 95 95ra73, 2011.
Kashmiri, Syed V.S., et al., "SDR grafting—a new approach to antibody humanization", Methods, vol. 36, pp. 25-34, (2005).
Klimka, A. , et al., "Human anti-CD30 recombinant antibodies by guided phage antibody selection using cell panning". British Journal of Cancer, vol. 83, No. 2, pp. 252-260, (2000).
Krause, Anja , et al., "Antigen-dependent CD28 Signaling Selectively Enhances Survival and Proliferation in Genetically Modified Activated Human Primary T Lymphocytes", The Journal of experimental medicine vol. 188,4 (1998): 619-26. doi:10.1084/jem.188.4.619.

(Continued)

*Primary Examiner* — Anand U Desai
*Assistant Examiner* — Amber K Faust
(74) *Attorney, Agent, or Firm* — Allogene Therapeutics, Inc.

(57) ABSTRACT

Provided herein are formulations and drug product processes that can improve cell viability and minimize waste of the manufactured formulated cells for a drug product.

20 Claims, 15 Drawing Sheets

(56) References Cited

OTHER PUBLICATIONS

Li, Rui , et al., "Preservation of cell-based immunotherapies for clinical trials", Cytotherapy; Sep. 2019; 21(9): 943-957; doi: 10.1016/j.jcyt.2019.07.004.

Lonberg, Nils , "Fully human antibodies from transgenic mouse and phage display platforms", Current Opinion in Immunology, 2008, 20:450-459.

Mahadevan, M. , et al., "Effect of Cooling, Freezing and Thawing Rates and Storage Conditions on Preservation of Human Spermatozoa", Andrologia; Jan.-Feb. 1984;16(1):52-60. doi: 10.1111/j.1439-0272.1984.tb00234.x.

Mirzapour, Tooba , et al., "Evaluation of the effects of cryopreservation on viability, proliferation and colony formation of human spermatogonial stem cells in vitro culture", Andrologia; Feb. 2013;45(1):26-34; Andrologia Feb. 2013;45(1):26-34.

Morrison, Sherie L., et al., "Chimeric human antibody molecules: Mouse antigen-binding domains with human constant region domains", Proc. Natl. Acad. Sci., USA, vol. 81, pp. 6851-6855, (1984).

Osbourn, Jane , et al., "From rodent reagents to human therapeutics using antibody guided selection", Methods, vol. 36, pp. 61-68, (2005).

Padlan, Eduardo A., et al., "A Possible Procedure for Reducing the Immunogenicity of Antibody Variable Domains While Preserving Their Ligand-Binding Properties", Mol. Immunol, vol. 28, pp. 489-498, (1991).

Pi, Chia-Hsing , et al., "Characterizing modes of action and interaction for multicomponent osmolyte solutions on Jurkat cells", Biotechnology and bioengineering; vol. 116, Issue3; Mar. 2019; pp. 631-643.

Porter, David L., et al., "Chimeric Antigen Receptor-Modified T Cells in Chronic Lymphoid Leukemia", N Engl J Med 2011;365:725-33.

Queen, Cary , et al., "A humanized antibody that binds to the interleukin 2 receptor", Proc. Natl. Acad. Sci. USA, vol. 86, pp. 10029-10033, (1989).

Riechmann, Lutz , et al., "Reshaping human antibodies for therapy", Nature, vol. 332, pp. 323-327, (1988).

Sethi, Dalip , et al., "De-risking the final formulation, fill and finish step in cell therapy manufacturing: considerations for an automated solution", Cell & Gene Therapy Insights 2020; 6(10), 1513-1519.

Song, De-Gang , et al., "CD27 costimulation augments the survival and antitumor activity of redirected human T cells in vivo", Blood (2012) 119 (3): 696-706.

Terumo , "Finia Fill and Finish System for Cell Therapy Manufacturing", Terumo Blood and Cell Technologies Youtube video; Oct. 11, 2019; https://www.youtube.com/watch?v=whrMosfqfTU.

Van Dijk, Marc A., et al., "Human antibodies as next generation therapeutics", Curr Opin Chem Biol, vol. 5, No. 4, pp. 368-374, (2001).

* cited by examiner

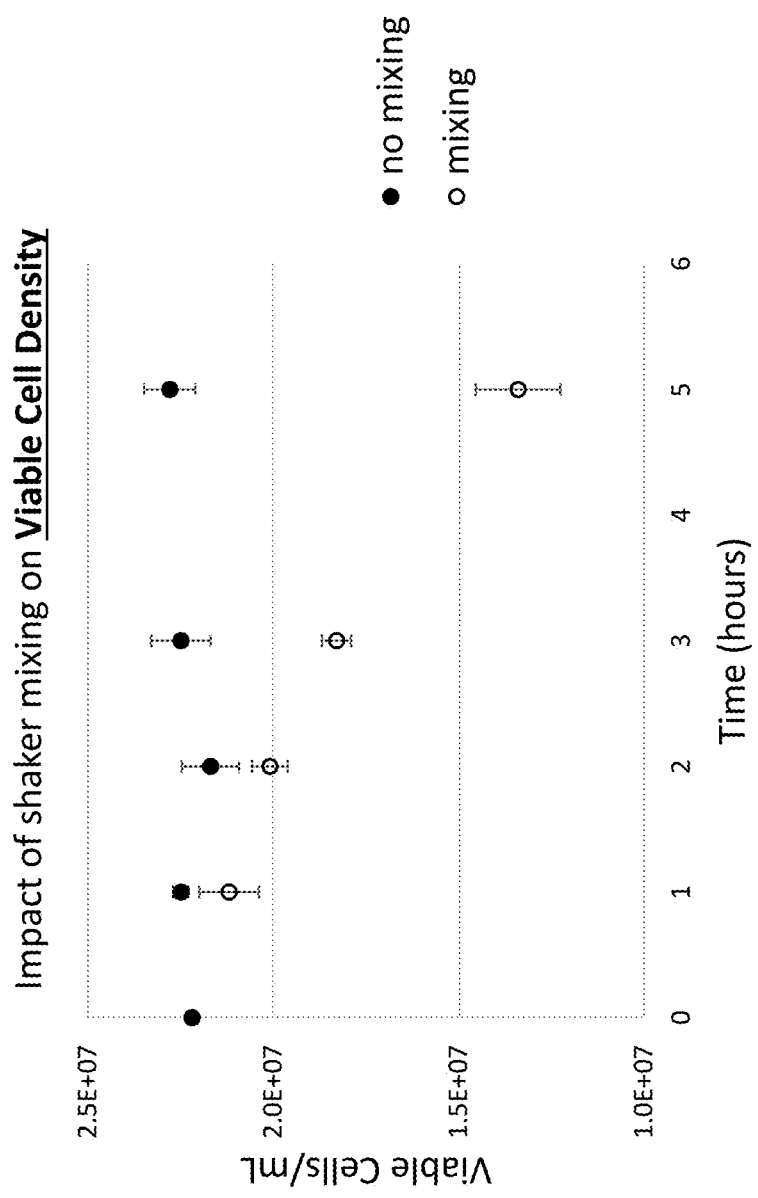

FORMULATIONS AND PROCESSES FOR CAR T CELL DRUG PRODUCTS

CROSS REFERENCE TO RELATED APPLICATIONS

The present application claims the benefit of priority to U.S. Provisional Application No. 63/145,235, filed Feb. 3, 2021, the content which is hereby incorporated by reference in its entirety.

FIELD

The instant disclosure relates to formulations and methods for processing cell-based drug products, including CAR T cell drug products.

BACKGROUND

The final steps of manufacturing engineered immune cells, such as CAR T cells, are the formulation and filling of active drug substance cells into one or more final containers, or the drug product process (the DP process). For example, after manufacturing, the cells are harvested from culture media by centrifugation, formulated in a composition that may contain a cryopreservative (such as Dimethylsulfoxide, DMSO). The formulated cells are filled into a suitable container closure system and may be frozen before being stored in vapor phase of liquid nitrogen (vLN2).

The DP process can be potentially stressful for the cells because, for example, the cells are removed from the culture media and culture conditions, and the formulation may contain a cryopreservative for storage (e.g., Dimethylsulfoxide, DMSO). DMSO is a strong solvent that may negatively affect cells in a time dependent manner. Additional sources of stress may come from physical shaking, mixing, and pumping of cells, and exposure of cells to room temperature or other non-cell culture conditions. The drug product process can take several hours depending on the batch size, and the cells need to be kept healthy and in suspension to ensure DP homogeneity. Thus, the consensus in the field was that time is a limiting factor in the drug product process and it would be important to minimize exposure time of cells to various stress conditions before freezing.

There is a need for a DP process that can improve cell viability and health and minimize wastage of the final drug product. This is particularly important for allogeneic cell drug products where a large number of cells for multiple doses can be produced in each batch of manufacturing.

SUMMARY

Provided herein are reagents and processes that can improve the viability and health of cells for use in cell-based therapies and minimize wastage in the manufacturing and drug product process.

Preserving cell viability during the formulation and filling process is critical and challenging. Optimizing formulation compositions and drug product processes are important for maintaining overall cell health and functionality. The instant disclosure provides improved formulations and/or processes that maintain better cell health and viability and allow sufficient time to complete the drug product process. It is especially advantageous for processing engineered cells, such as engineered immune cells, that can be produced in large batches in a drug product process to minimize wastage, while ensuring overall cell health and viability and uniformity of dosage content.

Thus, in one aspect, the present disclosure provides a drug product process that maintains cell health and/or homogeneity of cells. In certain embodiments, the present disclosure provides a drug product process of preparing a drug product comprising engineered immune cells, said method comprising the steps of formulating engineered immune cells in a composition containing a cryopreservative to form a drug product, and mixing and filling the drug product into one or more containers, wherein the drug product maintains homogeneity. In certain embodiments, the step of mixing and filling takes at least about two hours. In certain embodiments, the step of mixing and filling takes about two hours, about three hours, about four hours, about five hours or about 6 hours. In certain embodiments, the mixing comprises intermittent mixing. In some embodiments, the mixing comprises continuous mixing. In certain embodiments, the intermittent mixing is in a shaker flask. In certain embodiments, the intermittent mixing is in a spinner flask. In certain embodiments, the intermittent mixing comprises mixing for about 1 to about 3 minutes, about every 10 to about every 40 minutes. In certain embodiments, the mixing comprises continuous mixing in a spinner flask. In certain embodiments, the mixing comprises continuous mixing in a shaker flask for about two hours. In certain embodiments, the mixing comprises continuous mixing in a shaker flask for no more than two hours. In certain embodiments, the mixing comprises continuous mixing in a shaker flask for less than two hours.

In certain embodiments, the mixing and filling step is at about 4° C. In certain embodiments, the mixing and filling step is at room temperature. In certain embodiments, the mixing is at a speed of about 30 to about 85 rpm. In certain embodiments, the cryopreservative comprises DMSO or glycerol. In certain embodiments, the cryopreservative comprises about 3% DMSO to about 10% DMSO. In certain embodiments, the cryopreservative comprises about 5% DMSO. In certain embodiments, the composition further comprises an excipient that enhances viscosity. In certain embodiments, the engineered immune cells are T cells, inflammatory T-lymphocytes, cytotoxic T-lymphocytes, regulatory T-lymphocytes, helper T-lymphocytes, effector T-lymphocytes, tumor infiltrating lymphocytes (TILs), NK cells, NK-T-cells, TCR-expressing cells, TCR knockout T cells, dendritic cells, macrophages, killer dendritic cells, mast cells, or B-cells. In certain embodiments, the engineered immune cells are CAR T cells. In certain embodiments, the engineered immune cells are allogeneic CAR T cells. In certain embodiments, the engineered immune cells are autologous CAR T cells. In some embodiments, the engineered immune cells are human cells.

In another aspect, the instant disclosure provides a drug product comprising engineered immune cells prepared by the drug product process disclosed herein.

In yet another aspect, the instant disclosure provides methods of treating a subject in need of a treatment comprising administering to the subject the drug product disclosed herein. In certain embodiments, the subject is a human.

BRIEF DESCRIPTION OF THE DRAWINGS

FIGS. 2A-2B show impact of orbital shaker mixing of CAR T cell formulation on viable cell density (VCD) and cell viability.

The data in FIGS. 5A-5B compare the impact of continuous shaker flask mixing, intermittent shaker flask mixing with continuous spinner flask mixing on the VCD and viability of prefreeze CAR T drug product.

DETAILED DESCRIPTION

Figure 1:
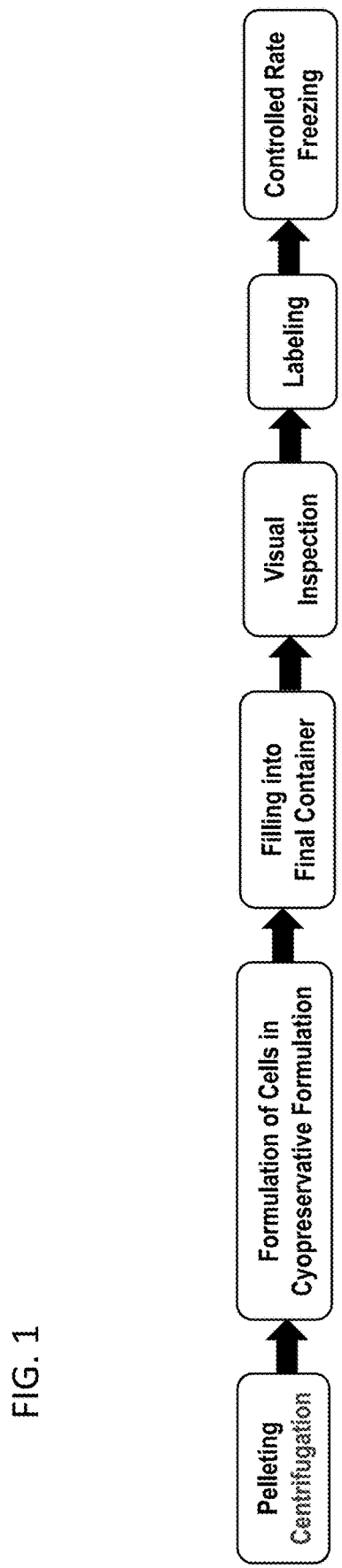
FIG. 1 shows an exemplary workflow of final steps of manufacturing of engineered cells for a drug product.

In one aspect, the instant disclosure provides formulations and methods for preparing and filling of a drug product. In one aspect, the instant disclosure provides a drug product process for a cell-based therapeutic, said drug product process allows sufficient time to finish filling or processing manufactured cell-based drug product while maintaining cell viability, and/or drug product homogeneity. In some embodiments, the drug product is a GMP drug product and/or produced in large quantities.

As used herein, the terms "a" and "an" are used to mean one or more. For example, a reference to "a cell" or "an antibody" means "one or more cells" or "one or more antibodies."

Drug product refers to a finished dosage form that contains a drug substance, generally, but not necessarily, in association with one or more other ingredients.

The drug product process refers to the final steps of GMP manufacturing, before the filled drug product is sent for, e.g., cryo-storage, liquid nitrogen storage, 4° C. storage or for direct use in patients.

The drug product process is critical in GMP manufacturing of cell-based therapeutics. The drug product process comprises harvesting manufactured cells from the optimal cell culture conditions and subjecting cells to conditions that can be stressful to cells. In the current process, the cells are constantly being mixed to ensure even distribution during the drug product process. Steps can be taken to minimize exposure of cells to stress conditions to ensure cell viability and cell product homogeneity to pass quality control. Controlling drug product filling time to minimize exposure of cells to stress conditions may sometimes lead to unfilled drug product that cannot be processed within the fill time window and unnecessary waste.

One source of stress is cell mixing during the drug product process. To keep the cells in suspension and prevent cell from settling, formulated cells are undergoing continuous mixing during the drug product process. In shaker flask mixing, formulated cells are placed in a shaker flask, for example an Erlenmeyer flask, which is then placed on a shaker or a shaker platform, such as an orbital shaker, to enable mixing. In contrast, a spinner flask is equipped with a mixing device, for example, a top mounted impeller or paddle with a stir bar, that enables internal mixing of contents in the spinner flask. Spinner flask mixing can occur when a spinner flask is placed on a magnetic stir plate and the paddle/stir bar rotates when driven by the magnetic force. Spinner flask mixing can also occur by other means, for example, driven by turning the impeller mechanically. Exemplary spinner flasks include, without limitation, Pyrex® ProCulture™ spinner flask, Corning® spinner flask, etc.

It was generally believed that shaker flask mixing is gentler to the cells than spinner flask mixing because, inter alia, unlike cells in a spinner flask, cells in a shaker flask are not in direct contact with a mixing device such as a paddle. As disclosed herein, it was surprisingly discovered that formulated cells maintain superior viability and viable cell density when the continuous mixing was performed in a spinner flask, as compared to a shaker flask.

Stress conditions in the drug product process can lead to cell death and further cause cell clumps and aggregates, all of which ultimately may affect the product quality, strength and potency of the drug product. Thus, in some embodiments, the present disclosure provides a process of preparing a drug product wherein the drug product maintains cell health and homogeneity.

Thus, in one aspect, the present disclosure provides a process of preparing a drug product comprising engineered immune cells, said method comprising the steps of formulating engineered immune cells in a composition containing a cryopreservative to form a drug product, and mixing and filling the drug product into one or more containers, wherein the drug product cell health and homogeneity are maintained.

Homogeneity of a cell-based drug product as used herein refers to a state of homogenous suspension of formulated cells in a composition without cell settling, clumping or aggregation. Maintaining homogeneity during the DP process of a cell-based drug product is important to ensure vial-to-vial consistency in cell viability and dosage concentration. Homogeneity can be evaluated by visual inspection. Homogeneity can also be ascertained by measuring and ensuring consistent cell concentration in each container with the filled cell-based drug product.

In some embodiments, the continuous mixing is conducted at about 30-80 rpm, about 30-85 rpm, about 25-85 rpm, about 35-80 rpm, about 35-85 rpm, about 40-80 rpm, about 40-85 rpm, about 45-80 rpm, about 45-85 rpm, about 50-80 rpm, about 50-85 rpm, about 55-80 rpm, about 55-85 rpm, about 60-80 rpm, about 60-85 rpm, about 65-80 rpm, about 65-85 rpm, about 70-80 rpm, about 70-85 rpm, about 75-80 rpm, about 75-85 rpm, about 25 rpm, about 30 rpm, about 35 rpm, about 40 rpm, about 45 rpm, about 50 rpm, about 55 rpm, about 60 rpm, about 65 rpm, about 70 rpm, about 75 rpm, about 80 rpm, or about 85 rpm.

In some embodiments, the cells are engineered immune cells. In some embodiments, the immune cells are CAR T cells. In some embodiments, the immune cells are CAR NK cells. In some embodiments, the immune cells are allogeneic or autologous immune cells. In some embodiments, the immune cells are autologous or allogeneic CAR T cells.

It was conventionally believed that during the drug product process the cells need to be mixed continuously to prevent settlement. As disclosed herein, it was unexpectedly discovered that continuous mixing during the drug product process is not required. Thus, in one aspect, the instant disclosure provides a drug product process comprising the step of intermittent mixing of cells. In some embodiments, the intermittent mixing is in a shaker flask. In certain embodiments, the intermittent mixing is in a spinner flask.

In some embodiments, the intermittent mixing is conducted at about 30-80 rpm, about 30-85 rpm, about 25-85 rpm, about 35-80 rpm, about 35-85 rpm, about 40-80 rpm, about 40-85 rpm, about 45-80 rpm, about 45-85 rpm, about 50-80 rpm, about 50-85 rpm, about 55-80 rpm, about 55-85 rpm, about 60-80 rpm, about 60-85 rpm, about 65-80 rpm, about 65-85 rpm, about 70-80 rpm, about 70-85 rpm, about 75-80 rpm, about 75-85 rpm, about 85-100 rpm, about 85-110 rpm, about 85-120 rpm, about 85-130 rpm, about 85-140 rpm, about 25 rpm, about 30 rpm, about 35 rpm, about 40 rpm, about 45 rpm, about 50 rpm, about 55 rpm, about 60 rpm, about 65 rpm, about 70 rpm, about 75 rpm, about 80 rpm, about 85 rpm, about 90 rpm, about 95 rpm, about 100 rpm, about 105 rpm, about 110 rpm, about 115 rpm, about 120 rpm, about 125 rpm, about 130 rpm, about 135 rpm, about 140 rpm, or about 145 rpm.

In some embodiments, the cells are engineered immune cells. In some embodiments, the immune cells are CAR T cells.

In some embodiments, the intermittent mixing is conducted for about 1-5 minutes, 1-4 minutes, 1-3 minutes, 1-2 minutes, one minute, or under one minute. In some embodiments, the intermittent mixing is conducted at an interval of about 10 to about 40 minutes. In some embodiments, the intermittent mixing is conducted at an interval of about every 10 to about every 40 minutes, about every 10 to about every 35 minutes, about every 10 to about every 30 minutes, about every 10 to about every 25 minutes, about every 10 to about every 20 minutes, about every 10 to about every 15 minutes, about every 10 to about every 45 minutes, about every 5 to about every 40 minutes, about every 4 minutes, about every 10 minutes, about every 15 minutes, about every 20 minutes, about every 25 minutes, about every 30 minutes, about every 35 minutes, about every 40 minutes, or about every 45 minutes.

In some embodiments, the one or more containers are sterile plastic or glass containers. In some embodiments, the one or more containers are plastic vials. In some embodiments, the one or more containers are glass vials. In some embodiments, the one or more containers are plastic bags.

In some embodiments, the cells are formulated in a composition comprising at least one cryopreservative (or cryoprotectant). Suitable cryopreservative includes, without limitation dimethylsulfoxide (DMSO), propylene glycol (PG), ethylene glycol (EG), glycerol, sucrose, and trehalose. In some embodiments, the cryopreservative present in the formulation or drug product is about 3% to about 10%, about 4% to about 10%, about 5% to about 10%, about 6% to about 10%, about 7% to about 10%, about 8% to about 10%, about 9% to about 10%, about 3%, about 4%, about 5%, about 6%, about 7%, about 8%, about 9%, or about 10%. In some embodiments, the cryopreservative is DMSO. In some embodiments the composition comprising a cryopreservative is, for example, Cryostor® CS10, CS2, CS5, CryoMACS DMSO or 2-8CELLsius™+DMSO.

In some embodiments, the formulation further comprises an excipient that enhances viscosity (or a viscosity enhancer). Suitable viscosity enhancer includes, without limitation, celluloses (e.g. methylcellulose, carboxymethyl cellulose, hydroxymethylcellulose, hydroxyenthylcellulose, hydroxypropylmethylcellulose), pectins, high molecular weight dextran (e.g., MW about 40 KDa to about 100 KDa, etc.), gelatin, hydroxyethyl starch, alginic acid, polyvinyl alcohol, polyvinylpyrrolidone, and other natural, semisynthetic or synthetic hydrocolloid. In some embodiments, the viscosity enhancer is present in the formulation at a concentration of about 0.1%-about 10%, about 0.1%-about 9%, about 0.1%-about 8%, about 0.1%-about 7%, about 0.1%-about 6%, about 0.1%-about 5%, about 0.1%-about 4%, about 0.1%-about 3%, about 0.1%-about 2%, or about 0.1%-about 1%. In some embodiments, the formulation has a viscosity of about 2-about 20 cps, about 2-about 19 cps, about 2-about 18 cps, about 2-about 17 cps, about 2-about 16 cps, about 2-about 15 cps, about 2-about 14 cps, about 2-about 13 cps, about 2-about 12 cps, about 2-about 11 cps, about 2-about 10 cps, about 2-about 9 cps, about 2-about 8 cps, about 2-about 7 cps, about 2-about 6 cps, or about 2-about 5 cps.

In some embodiments, the mixing and filling step takes about two hours. In some embodiments, the mixing and filling step takes less than about two hours. In some embodiments, the mixing and filling step takes at least about two hours. In some embodiments, the mixing and filling step takes longer than about two hours. In some embodiments, the mixing and filling step takes about three hours, longer than three hours, about four hours, longer than four hours, about five hours, about six hours, about seven hours, about eight hours, about nine hours, about ten hours, between about two to about three hours, between about two to about four hours, between about two to about five hours, between about two to about six hours, between about three to about six hours, or between about four to about six hours.

In some embodiments, the mixing and filling step is conducted at room temperature. In some embodiments, the mixing and filling step is conducted at about 15-20° C., about 20-25° C., about 20-27° C., about 20-30° C., or about 25-30° C. In some embodiments, the mixing and filling step is conducted at about 2-8° C. In some embodiments, the mixing and filling step is conducted at about 4-5° C.

In some embodiments, the drug product process comprises the step of mixing the formulated cells by continuous shaker flask mixing at room temperature for up to about two hours. In some embodiments, the drug product process comprises the step of mixing the formulated cells by intermittent shaker flask mixing at room temperature for up to about four or about six hours. In some embodiments, the speed in continuous or intermittent shaker flask mixing is no more than about 85 rpm. In some embodiments, the intermittent shaker flask mixing is for about 1-3 minutes about every 10-30 minutes. In some embodiments, the drug product process comprises the step of mixing the formulated cells by continuous spinner flask mixing at room temperature for up to about four or about six hours. In some embodiments, the drug product process comprises the step of mixing the formulated cells by intermittent spinner flask mixing at room temperature for up to about four or about six hours. In some embodiments, the speed in continuous or intermittent spinner flask mixing is at a speed of about 40 rpm. In some embodiments, the speed in continuous or intermittent spinner flask mixing is at a speed no more than about 40 rpm. In some embodiments, the intermittent spinner flask mixing is for about 1-3 minutes about every 10-30 minutes.

In some embodiments, the cells are engineered immune cells. In some embodiments, the immune cells are CAR T cells. In some embodiments, the immune cells are CAR NK cells. In some embodiments, the immune cells are allogeneic or autologous immune cells. In some embodiments, the immune cells are autologous or allogeneic CAR T cells.

Immune Cells

Cells suitable for use with the methods and/or reagents described herein include immune cells.

Prior to the in vitro manipulation or genetic modification (e.g., as described herein), cells for use in methods described herein (e.g., immune cells) can be obtained from a subject. Cells can be obtained from a number of non-limiting sources, including peripheral blood mononuclear cells, bone marrow, lymph node tissue, cord blood, thymus tissue, stem cell- or iPSC-derived immune cells, tissue from a site of infection, ascites, pleural effusion, spleen tissue, and tumors. In some embodiments, any number of T cell lines available and known to those skilled in the art, can be used. In some embodiments, cells can be derived from a healthy donor, from a patient diagnosed with cancer or from a patient diagnosed with an infection. In some embodiments, cells can be part of a mixed population of cells which present different phenotypic characteristics.

In some embodiments, immune cells are autologous immune cells obtained from a subject who will ultimately receive the engineered immune cells. In some embodiments, immune cells are allogeneic immune cells obtained from a donor, who is a different individual from the subject who will receive the engineered immune cells.

In some embodiments, immune cells comprise T cells. T cells can be obtained from a number of sources, including peripheral blood mononuclear cells (PBMCs), bone marrow, lymph nodes tissue, cord blood, thymus tissue, stem cell- or iPSC-derived T cells, tissue from a site of infection, ascites, pleural effusion, spleen tissue, and tumors. In some embodiments, T cells can be obtained from a volume of blood collected from the subject using any number of techniques known to the skilled person, such as FICOLL™ separation.

Cells can be obtained from the circulating blood of an individual by apheresis. The apheresis product typically contains lymphocytes, including T cells, monocytes, granulocytes, B cells, other nucleated white blood cells, red blood cells, and platelets. In some embodiments, the cells collected by apheresis can be washed to remove the plasma fraction, and placed in an appropriate buffer or media for subsequent processing.

PBMCs can be used directly for genetic modification with the immune cells (such as CARs or TCRs) using methods as described herein. In certain embodiments, after isolating the PBMCs, T lymphocytes can be further isolated and both cytotoxic and helper T lymphocytes can be sorted into naive, memory, and effector T cell subpopulations either before or after genetic modification and/or expansion.

In certain embodiments, T cells are isolated from PBMCs by lysing the red blood cells and depleting the monocytes, for example, using centrifugation through a PERCOLL™ gradient. A specific subpopulation of T cells, such as CCR7+, CD95+, CD122, CD27+, CD69+, CD127+, CD28+, CD3+, CD4+, CD8+, CD25+, CD62L+, CD45RA+, and CD45RO+ T cells can be further isolated by positive or negative selection techniques known in the art. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting can also be used to isolate cell populations of interest for use in the present disclosure.

In some embodiments, a population of T cells is enriched for CD4+ cells.

In some embodiments, a population of T cells is enriched for CD8+ cells.

In some embodiments, CD8+ cells are further sorted into naive, central memory, and effector cells by identifying cell surface antigens that are associated with each of these types of cells. In some embodiments the expression of phenotypic markers for naïve T cells include CD45RA+, CD95−, IL2Rβ−, CCR7+, and CD62L+. In some embodiments the expression of phenotypic markers for stem cell memory T cells include CD45RA+, CD95+, IL2Rβ+, CCR7+, and CD62L+. In some embodiments the expression of phenotypic markers for central memory T cells include CD45RO+, CD95+, IL2Rβ+, CCR7+, and CD62L+. In some embodiments the expression of phenotypic markers for effector memory T cells include CD45RO+, CD95+, IL2Rβ+, CCR7−, and CD62L−. In some embodiments the expression of phenotypic markers for T effector cells include CD45RA+, CD95+, IL2RB+, CCR7−, and CD62L−. Thus, CD4+ and/or CD8+ T helper cells can be sorted into naive, stem cell memory, central memory, effector memory and T effector cells by identifying cell populations that have cell surface antigens.

It will be appreciated that PBMCs can further include other cytotoxic lymphocytes such as NK cells or NKT cells. An expression vector carrying the coding sequence of a chimeric receptor as disclosed herein can be introduced into a population of human donor T cells, NK cells or NKT cells. Standard procedures are used for cryopreservation of T cells expressing the CAR for storage and/or preparation for use in a human subject. In one embodiment, the in vitro transduction, culture and/or expansion of T cells are performed in the absence of non-human animal derived products such as fetal calf serum and fetal bovine serum. In various embodiments a cryopreservative media can comprise, for example, CryoStor® CS2, CS5, or CS10 or other medium comprising DMSO, or a medium that does not comprise DMSO.

Engineered Immune Cells

Provided herein are engineered immune cells expressing the CARs of the disclosure (e.g., CAR-T cells).

In some embodiments, an engineered immune cell comprises a population of CARs, each CAR comprising extracellular antigen-binding domains. In some embodiments, an engineered immune cell comprises a population of CARs, each CAR comprising different extracellular antigen-binding domains. In some embodiments, an immune cell comprises a population of CARs, each CAR comprising the same extracellular antigen-binding domains.

The engineered immune cells can be allogeneic or autologous.

In some embodiments, the engineered immune cell is a T cell (e.g., inflammatory T-lymphocyte, cytotoxic T-lymphocyte, regulatory T-lymphocyte, helper T-lymphocyte, or tumor infiltrating lymphocyte (TIL)), NK cell, NK-T-cell, TCR-expressing cell, dendritic cell, killer dendritic cell, a mast cell, or a B-cell. In some embodiments, the cell can be derived from the group consisting of CD4+ T-lymphocytes and CD8+ T-lymphocytes. In some exemplary embodiments, the engineered immune cell is a T cell. In some exemplary embodiments, the engineered immune cell is an alpha beta T cell. In some exemplary embodiments, the engineered immune cell is a gamma delta T cell. In some exemplary embodiments, the engineered immune cell is a macrophage. In some embodiments, the engineered immune cells are human cells.

In some embodiments, the engineered immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells (iPSC), totipotent stem cells or hematopoietic stem cells. Stem cells can be CD34+ or CD34−.

In some embodiments, the cell is obtained or prepared from peripheral blood. In some embodiments, the cell is obtained or prepared from peripheral blood mononuclear cells (PBMCs). In some embodiments, the cell is obtained or prepared from bone marrow. In some embodiments, the cell is obtained or prepared from umbilical cord blood. In some embodiments, the cell is a human cell. In some embodiments, the cell is transfected or transduced by the nucleic acid vector using a method selected from the group consisting of electroporation, sonoporation, biolistics (e.g., Gene Gun), transfection, lipid transfection, polymer transfection, nanoparticles, viral transduction or viral transfection (e.g., retrovirus, lentivirus, AAV) or polyplexes. In some embodiments the cell is a T cell that has been re-programmed from a non-T cell. In some embodiments the cell is a T cell that has been re-programmed from a T cell.

Binding Agents

In embodiments, the disclosed methods comprise the use of an antibody or antigen binding agent (e.g., comprising an antigen binding domain or comprising an antibody or fragment thereof). As discussed below, in various embodiments engineered immune cells can also comprise a binding agent.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain. Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence.

Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation.

For purposes of the instant disclosure, in certain embodiments, any polypeptide or complex of polypeptides that includes sufficient immunoglobulin domain sequences as found in natural antibodies can be referred to and/or used as an "antibody," whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art.

Moreover, the term "antibody" as used herein, can refer to any of the art-known or developed constructs or formats for utilizing antibody structural and functional features in alternative presentation. For example, in some embodiments, an antibody utilized in the methods of the instant disclosure is in a format selected from, but not limited to, intact IgA, IgG, IgE or IgM antibodies; bi- or multi-specific antibodies (e.g., Zybodies®, etc.); antibody fragments such as Fab fragments, Fab fragments, F(ab)2 fragments, Fd fragments, and isolated CDRs or sets thereof; single chain variable fragments (scFVs); polypeptide-Fc fusions; single domain antibodies (e.g., shark single domain antibodies such as IgNAR or fragments thereof); camelid antibodies (also referred to herein as nanobodies or VHHs); shark antibodies, masked antibodies (e.g., Probodies®); Small Modular ImmunoPharmaceuticals (SMIPs™); single chain or Tandem diabodies (TandAb®); VHHs; Anticalins®; Nanobodies® minibodies; BiTE®s; ankyrin repeat proteins or DARPINS®; Avimers®; DARTs; TCR-like antibodies;, Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload (e.g., a detectable moiety, a therapeutic moiety, a catalytic moiety, etc.), or other pendant group (e.g., poly-ethylene glycol, etc.).

As used herein, the term "antibody agent" generally refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc. as is known in the art. In many embodiments, the term "antibody agent" is used to refer to one or more of the art-known or developed constructs or formats for utilizing antibody structural and functional features in alternative presentation. For example, an antibody agent utilized in accordance with the present invention is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals (SMIPs™); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®S.

An antibody or antibody agent used in performing the methods of the instant disclosure can be single chained or double chained. In some embodiments, the antibody or antigen binding molecule is single chained. In certain embodiments, the antigen binding molecule is selected from the group consisting of an scFv, a Fab, a Fab', a Fv, a F(ab')$_2$, a dAb, and any combination thereof.

Antibodies and antibody agents include antibody fragments. An antibody fragment comprises a portion of an intact antibody, such as the antigen binding or variable region of the intact antibody. Antibody fragments include, but are not limited to, Fab, Fab', Fab'-SH, F(ab') 2, Fv, diabody, linear antibodies, multispecific formed from antibody fragments antibodies and scFv fragments, and other fragments. Antibodies also include, but are not limited to, polyclonal monoclonal, chimeric dAb (domain antibody), single chain, Fab, Fa, F(ab')$_2$ fragments, and scFvs. An antibody can be a whole antibody, or immunoglobulin, or an antibody fragment. Antibody fragments can be made by various techniques, including but not limited to proteolytic digestion of an intact antibody as well as production by recombinant host cells (e.g., E. coli, Chinese Hamster Ovary (CHO) cells, or phage), as known in the art.

In some embodiments, an antibody or antibody agent can be a chimeric antibody (see, e.g., U.S. Pat. No. 4,816,567; and Morrison et al., Proc. Natl. Acad. Sci. USA, 81:6851-6855 (1984)). A chimeric antibody can be an antibody in which a portion of the heavy and/or light chain is derived from a particular source or species, while the remainder of the heavy and/or light chain is derived from a different source or species. In one example, a chimeric antibody can comprise a non-human variable region (e.g., a variable region derived from a mouse, rat, hamster, rabbit, or non-human primate, such as a monkey) and a human constant region. In a further example, a chimeric antibody can be a "class switched" antibody in which the class or subclass has been changed from that of the parent antibody. Chimeric antibodies include antigen-binding fragments thereof.

In some embodiments, a chimeric antibody can be a humanized antibody (See, e.g., Almagro and Fransson, Front. Biosci., 13:1619-1633 (2008); Riechmann et al., Nature, 332:323-329 (1988); Queen et al., Proc. Natl Acad. Sci. USA 86:10029-10033 (1989); U.S. Pat. Nos. 5,821,337, 7,527,791, 6,982,321, and 7,087,409; Kashmiri et al., Methods 36:25-34 (2005); Padlan, Mol. Immunol, 28:489-498 (1991); Dall'Acqua et al., Methods, 36:43-60 (2005); Osbourn et al., Methods, 36:61-68 (2005); and Klimka et al., Br. J. Cancer, 83:252-260 (2000)). A humanized antibody is a chimeric antibody comprising amino acid residues from non-human hypervariable regions and amino acid residues from human FRs. In certain embodiments, a humanized antibody will comprise substantially all of at least one, and typically two, variable domains, in which all or substantially all of the hypervariable regions (e.g., CDRs) correspond to those of a non-human antibody, and all or substantially all of the Framework Regions (FRs) correspond to those of a human antibody. A humanized antibody optionally can comprise at least a portion of an antibody constant region derived from a human antibody.

In some embodiments, an antibody or antibody agent provided herein is a human antibody. Human antibodies can be produced using various techniques known in the art (See, e.g., van Dijk and van de Winkel, Curr. Opin. Pharmacol, 5:368-74 (2001); and Lonberg, Curr. Opin. Immunol, 20:450-459 (2008)). A human antibody can be one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies may be prepared using methods well known in the art.

Chimeric Antigen Receptors

As used herein, chimeric antigen receptors (CARs) are proteins that specifically recognize target antigens (e.g., target antigens on cancer cells). When bound to the target antigen, the CAR can activate the immune cell to attack and destroy the cell bearing that antigen (e.g., the cancer cell). CARs can also incorporate costimulatory or signaling domains to increase their potency. See Krause et al., J. Exp. Med., Volume 188, No. 4, 1998 (619-626); Finney et al., *Journal of Immunology*, 1998, 161:2791-2797, Song et al., Blood 119:696-706 (2012); Kalos et al., *Sci. Transl. Med.* 3:95 (2011); Porter et al., *N. Engl. J. Med.* 365:725-33 (2011), and Gross et al., *Annu. Rev. Pharmacol. Toxicol.* 56:59-83 (2016); U.S. Pat. Nos. 7,741,465, and 6,319,494.

Chimeric antigen receptors described herein comprise an extracellular domain, a transmembrane domain, and an intracellular domain, wherein the extracellular domain comprises an antigen binding domain that specifically binds to the target.

In some embodiments, antigen-specific CARs further comprise a safety switches and/or one or more monoclonal antibody specific-epitope.

i. Antigen Binding Domains

As discussed above, CARs described herein comprise an antigen binding domain. An "antigen binding domain" as used herein means any polypeptide that binds a specified target antigen. In some embodiments, the antigen binding domain binds to an antigen on a tumor cell. In some embodiments, the antigen binding domain binds to an antigen on a cell involved in a hyperproliferative disease.

In some embodiments, the antigen binding domain comprises a variable heavy chain, variable light chain, and/or one or more CDRs described herein. In some embodiments, the antigen binding domain is a single chain variable fragment (scFv), comprising light chain CDRs CDR1, CDR2 and CDR3, and heavy chain CDRs CDR1, CDR2 and CDR3.

An antigen binding domain is said to be "selective" when it binds to one target more tightly or with higher affinity than it binds to a second target.

The antigen binding domain of the CAR selectively targets a cancer antigen. In some embodiments, the cancer antigen is selected from EGFRvIII, WT-1, CD20, CD23, CD30, CD38, CD33, CD133, MHC-WT1, TSPAN10, MHC-PRAME, Liv1, ADAM10, CHRNA2, LeY, NKGD2D, CS1, CD44v6, ROR1, Claudin-18.2, Muc17, FAP alpha, Ly6G6D, c6orf23, G6D, MEGT1, NG25, CD19, BCMA, FLT3, CD70, DLL3, CD52 or CD34. In some embodiments, the CAR comprises an antigen binding domain that targets EGFRVIII, WT-1, CD20, CD23, CD30, CD38, CD33, CD133, MHC-WT1, TSPAN10, MHC-PRAME, Liv1, ADAM10, CHRNA2, LeY, NKGD2D, CS1, CD44v6, ROR1, Claudin-18.2, Muc17, FAP alpha, Ly6G6D, c6orf23, G6D, MEGT1, NG25, CD19, BCMA, FLT3, CD70, DLL3, CD52 or CD34.

In some embodiments, the cancer antigen is selected from the group consisting of carbonic anhydrase IX (CAIX), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein (EGP 2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptors, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Ra2), κ-light chain, kinase insert domain receptor (KDR), Lewis A (CA19.9),, LI cell adhesion molecule (LICAM), melanoma antigen family A, 1 (MAGE-AI), Mucin 16 (Muc-16), Mucin 1 (Muc-1), Mesothelin (MSLN), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), and Wilms tumor protein (WT-1).

Variants of the antigen binding domains (e.g., variants of the CDRs, VH and/or VL) are also within the scope of the disclosure, e.g., variable light and/or variable heavy chains that each have at least 70-80%, 80-85%, 85-90%, 90-95%, 95-97%, 97-99%, or above 99% identity to the amino acid sequences of antigen binding domain sequences. In some instances, such molecules include at least one heavy chain and one light chain, whereas in other instances the variant forms contain two variable light chains and two variable heavy chains (or subparts thereof). A skilled artisan will be able to determine suitable variants of the antigen binding domains as set forth herein using well-known techniques. In certain embodiments, one skilled in the art can identify suitable areas of the molecule that can be changed without destroying activity by targeting regions not believed to be important for activity.

In some embodiments, the polypeptide structure of the antigen binding domains is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen binding domain comprises or consists of avimers.

In some embodiments, an antigen binding domain is a scFv. In some embodiments, an antigen-selective CAR comprises a leader or signal peptide.

In other embodiments, the disclosure relates to isolated polynucleotides encoding any one of the antigen binding domains described herein. In some embodiments, the disclosure relates to isolated polynucleotides encoding a CAR. Also provided herein are vectors comprising the polynucleotides, and methods of making same.

In other embodiments, the disclosure relates to isolated polynucleotides encoding any one of the antigen binding domains described herein. In some embodiments, the disclosure relates to isolated polynucleotides encoding a CAR. Also provided herein are vectors comprising the polynucleotides, and methods of making same.

In some embodiments, a CAR-immune cell (e.g., CAR-T cell) which can form a component of a population of cells generated by practicing the methods of the instant disclosure comprises a polynucleotide encoding a safety switch polypeptide, such as for example RQR8. See, e.g., WO2013153391A, which is hereby incorporated by reference in its entirety. In a CAR-immune cell (e.g., a CAR-T cell) comprising the polynucleotide, the safety switch polypeptide can be expressed at the surface of a CAR-immune cell (e.g., CAR-T cell).

ii. Hinge Domain

The extracellular domain of the CARs of the disclosure can comprise a "hinge" domain (or hinge region). The term generally refers to any polypeptide that functions to link the transmembrane domain in a CAR to the extracellular antigen binding domain in a CAR. In particular, hinge domains can be used to provide more flexibility and accessibility for the extracellular antigen binding domain.

A hinge domain can comprise up to 300 amino acids—in some embodiments 10 to 100 amino acids or in some embodiments 25 to 50 amino acids. The hinge domain can be derived from all or part of naturally occurring molecules, such as from all or part of the extracellular region of CD8, CD4, CD28, 4-1BB, or IgG (in particular, the hinge region of an IgG; it will be appreciated that the hinge region can contain some or all of a member of the immunoglobulin family such as IgG1, IgG2, IgG3, IgG4, IgA, IgD, IgE, IgM, or fragment thereof), or from all or part of an antibody heavy-chain constant region. Alternatively, the hinge domain can be a synthetic sequence that corresponds to a naturally occurring hinge sequence, or can be an entirely synthetic hinge sequence. In some embodiments said hinge domain is a part of human CD8a chain (e.g., NP_001139345.1). In other embodiments, said hinge and transmembrane domains comprise a part of human CD8a chain. In some embodiments, the hinge domain of CARs described herein comprises a subsequence of CD8a, an IgG1, IgG4, PD-1 or an FcγRIIIα, in particular the hinge region of any of an CD8α, an IgG1, IgG4, PD-1 or an FcγRIIIα. In some embodiments, the hinge domain comprises a human CD8a hinge, a human IgG1 hinge, a human IgG4, a human PD-1 or a human FcγRIIIα hinge. In some embodiments the CARs disclosed herein comprise a scFv, CD8α human hinge and transmembrane domains, the CD3ζ signaling domain, and 4-1BB signaling domain.

iii. Transmembrane Domain

The CARs of the disclosure are designed with a transmembrane domain that is fused to the extracellular domain of the CAR. It can similarly be fused to the intracellular domain of the CAR. In some instances, the transmembrane domain can be selected or modified by amino acid substitution to avoid binding of such domains to the transmembrane domains of the same or different surface membrane proteins to minimize interactions with other members of the receptor complex. In some embodiments, short linkers can form linkages between any or some of the extracellular, transmembrane, and intracellular domains of the CAR.

Suitable transmembrane domains for a CAR disclosed herein have the ability to (a) be expressed at the surface an immune cell such as, for example without limitation, a lymphocyte cell, such as a T helper ($T_h$) cell, cytotoxic T ($T_c$) cell, T regulatory ($T_{reg}$) cell, or Natural killer (NK) cells, and/or (b) interact with the extracellular antigen binding domain and intracellular signaling domain for directing the cellular response of an immune cell against a target cell.

The transmembrane domain can be derived either from a natural or from a synthetic source. Where the source is natural, the domain can be derived from any membrane-bound or transmembrane protein.

Transmembrane regions of particular use in this disclosure can be derived from (comprise, or correspond to) CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

As non-limiting examples, the transmembrane region can be derived from, or be a portion of a T cell receptor such as α, β, γ or δ, polypeptide constituting CD3 complex, IL-2 receptor p55 (α chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1).

In some embodiments, the transmembrane domain in the CAR of the disclosure is a CD8α transmembrane domain.

In some embodiments, the transmembrane domain in the CAR of the disclosure is a CD28 transmembrane domain.

iv. Intracellular Domain

The intracellular (cytoplasmic) domain of the CARs of the disclosure can provide activation of at least one of the normal effector functions of the immune cell comprising the CAR. Effector function of a T cell, for example, can refer to cytolytic activity or helper activity, including the secretion of cytokines.

In some embodiments, an activating intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability.

It will be appreciated that suitable (e.g., activating) intracellular domains include, but are not limited to signaling domains derived from (or corresponding to) CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1 1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

The intracellular domains of the CARs of the disclosure can incorporate, in addition to the activating domains described above, co-stimulatory signaling domains (interchangeably referred to herein as costimulatory molecules) to increase their potency. Costimulatory domains can provide a signal in addition to the primary signal provided by an activating molecule as described herein.

It will be appreciated that suitable costimulatory domains within the scope of the disclosure can be derived from (or correspond to) for example, CD28, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 1a/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNFR, integrin, signaling lymphocytic activation molecule, BTLA, Toll ligand receptors, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. It will be appreciated that additional costimulatory molecules, or fragments thereof, not listed above are within the scope of the disclosure.

In some embodiments, the intracellular/cytoplasmic domain of the CAR can be designed to comprise the 4-1BB/CD137 domain by itself or combined with any other desired intracellular domain(s) useful in the context of the CAR of the disclosure. The complete native amino acid sequence of 4-1BB/CD137 is described in NCBI Reference Sequence: NP_001552.2. The complete native 4-1BB/CD137 nucleic acid sequence is described in NCBI Reference Sequence: NM_001561.5.

In some embodiments, the intracellular/cytoplasmic domain of the CAR can be designed to comprise the CD28 domain by itself or combined with any other desired intracellular domain(s) useful in the context of the CAR of the disclosure. The complete native amino acid sequence of CD28 is described in NCBI Reference Sequence: NP_006130.1. The complete native CD28 nucleic acid sequence is described in NCBI Reference Sequence: NM_006139.1.

In some embodiments, the intracellular/cytoplasmic domain of the CAR can be designed to comprise the CD3 zeta domain by itself or combined with any other desired intracellular domain(s) useful in the context of the CAR of the disclosure.

For example, the intracellular domain of the CAR can comprise a CD3 zeta chain portion and a portion of a costimulatory signaling molecule. The intracellular signaling sequences within the intracellular signaling portion of the CAR of the disclosure can be linked to each other in a random or specified order. In some embodiments, the intracellular domain is designed to comprise the activating domain of CD3 zeta and a signaling domain of CD28. In some embodiments, the intracellular domain is designed to comprise the activating domain of CD3 zeta and a signaling domain of 4-1BB.

In some embodiments the intracellular signaling domain of the CAR of the disclosure comprises a domain of a co-stimulatory molecule. In some embodiments, the intracellular signaling domain of a CAR of the disclosure comprises a part of co-stimulatory molecule selected from the group consisting of fragment of 4-1BB (GenBank: AAA53133.) and CD28 (NP_006130.1).

Genetic Modifications of CAR T Cells

Also provided herein are engineered immune cells and populations of engineered immune cells expressing CAR (e.g., CAR-T cells or CAR+ cells), which are depleted of cells expressing endogenous TCR.

In some embodiments, an engineered immune cell comprises a CAR T cell, each CAR T cell comprising an extracellular antigen-binding domain and has reduced or eliminated expression of endogenous TCR. In some embodiments, a population of engineered immune cells comprises a population of CAR T cells, each CAR T cell comprising two or more different extracellular antigen-binding domain and has reduced or eliminated expression of endogenous TCR. In some embodiments, an immune cell comprises a population of CARs, each CAR T cell comprising the same extracellular antigen-binding domains and has reduced or eliminated expression of endogenous TCR.

In some embodiments, an engineered immune cell according to the present disclosure comprises one disrupted or inactivated gene selected from the group consisting of CD52, DLL3, GR, PD-1, CTLA-4, LAG3, TIM3, BTLA, BY55, TIGIT, B7H5, LAIR1, SIGLEC10, 2B4, HLA, TCRα and TCRβ and/or expresses a CAR, a multi-chain CAR and/or a pTα transgene. In some embodiments, an isolated cell comprises polynucleotides encoding polypeptides comprising a multi-chain CAR. In some embodiments, the isolated cell according to the present disclosure comprises two disrupted or inactivated genes selected from the group consisting of: CD52 and GR, CD52 and TCRα, CDR52 and TCRβ, DLL3 and CD52, DLL3 and TCRα, DLL3 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, TIM3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ and/or expresses a CAR, including a multi-chain CAR, and/or a pTα transgene. In some embodiments the method comprises disrupting or inactivating one or more genes by introducing into the cells an endonuclease capable of selectively inactivating a gene by selective DNA cleavage. In some embodiments the endonuclease can be, for example, a zinc finger nuclease (ZFN), megaTAL nuclease, meganuclease, transcription activator-like effector nuclease (TALE-nuclease, or TALEN®), or CRISPR (e.g., Cas9 or Cas12) endonuclease.

In some embodiments, TCR is rendered not functional in the cells according to the disclosure by disrupting or inactivating TCRα gene and/or TCRß gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, susceptible to be obtained by this method are encompassed in the scope of the present disclosure. Modified cells disclosed herein can be used for treating patients in need thereof against Host versus Graft (HvG) rejection and Graft versus Host Disease (GvHD); therefore in the scope of the present disclosure is a method of treating patients in need thereof against Host versus Graft (HvG) rejection and Graft versus Host Disease (GvHD) comprising treating said patient by administering to said patient an effective amount of modified cells comprising disrupted or inactivated TCRα and/or TCRβ genes.

The present disclosure provides methods of determining the purity of a population of engineered immune cells lacking or having reduced endogenous TCR expression. In some embodiments, the engineered immune cells comprise less than 5.0%, less than 4.0%, less than 3.0% TCR+ cells, less than 2.0% TCR+ cells, less than 1.0% TCR+ cells, less than 0.9% TCR+ cells, less than 0.8% TCR+ cells, less than 0.7% TCR+ cells, less than 0.6% TCR+ cells, less than 0.5% TCR+ cells, less than 0.4% TCR+ cells, less than 0.3% TCR+ cells, less than 0.2% TCR+ cells, or less than 0.1% TCR+ cells. Such a population can be a product of the disclosed methods.

In some embodiments, an engineered immune cell according to the present disclosure can comprise one or more disrupted or inactivated genes. In some embodiments, a gene for a target antigen (e.g., EGFRvIII, Flt3, WT-1, CD20, CD23, CD30, CD38, CD33, CD133, MHC-WT1, TSPAN10, MHC-PRAME, Liv1, ADAM10, CHRNA2, LeY, NKGD2D, CS1, CD44v6, ROR1, Claudin-18.2, Muc17, FAP alpha, Ly6G6D, c6orf23, G6D, MEGT1, NG25, CD19, BCMA, FLT3, CD70, DLL3, or CD34, CD70) can be knocked out to introduce a CAR targeting the same antigen (e.g., a EGFRvIII, Flt3, WT-1, CD20, CD23, CD30, CD38, CD33, CD133, MHC-WT1, TSPAN10, MHC-PRAME, Liv1, ADAM10, CHRNA2, LeY, NKGD2D, CS1, CD44v6, ROR1, Claudin-18.2, Muc17, FAP alpha, Ly6G6D, c6orf23, G6D, MEGT1, NG25, CD19, BCMA, FLT3, CD70, DLL3, or CD34, CD70 CAR) to avoid induced CAR activation. As described herein, in some embodiments, an engineered immune cell according to the present disclosure comprises one disrupted or inactivated gene selected from the group consisting of MHC1 (B2M), MHC2 (CIITA), EGFRVIII, Flt3, WT-1, CD20, CD23, CD30, CD38, CD33, CD133, MHC-WT1, TSPAN10, MHC-PRAME, Liv1, ADAM10, CHRNA2, LeY, NKGD2D, CS1, CD44v6, ROR1, Claudin-18.2, Muc17, FAP alpha, Ly6G6D, c6orf23, G6D, MEGT1, NG25, CD19, BCMA, FLT3, CD70, DLL3, or CD34, CD70, TCRα and TCRβ and/or expresses a CAR or a multi-chain CAR. In some embodiments, a cell comprises a multi-chain CAR. In some embodiments, the isolated cell comprises two disrupted or inactivated genes selected from the group consisting of: CD52 and TCRα, CDR52 and TCRβ, PD-1 and TCRα, PD-1 and TCRβ, MHC-1 and TCRα, MHC-1 and TCRβ, MHC2 and TCRα, MHC2 and TCRβ and/or expresses a CAR or a multi-chain CAR.

The engineered immune cells can be allogeneic or autologous.

In some embodiments, an engineered immune cell or population of engineered immune cells comprises a T cell (e.g., inflammatory T-lymphocyte, cytotoxic T-lymphocyte, regulatory T-lymphocyte, helper T-lymphocyte, tumor infiltrating lymphocyte (TIL)), NK cell, NK-T-cell, TCR-expressing cell, dendritic cell, killer dendritic cell, a mast cell, or a B-cell, and expresses a CAR. In some embodiments, the T cell can be derived from the group consisting of CD4+ T lymphocytes, CD8+ T lymphocytes or population comprising a combination of CD4+ and CD8+ T cells.

In some embodiments, an engineered immune cell or population of engineered immune cells that are generated using the disclosed methods can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells.

In some embodiments, an engineered immune cell or a population of immune cells that are generated using the disclosed methods is obtained or prepared from peripheral blood. In some embodiments, an engineered immune cell is obtained or prepared from peripheral blood mononuclear cells (PBMCs). In some embodiments, an engineered immune cell is obtained or prepared from bone marrow. In some embodiments, an engineered immune cell is obtained or prepared from umbilical cord blood. In some embodiments, the cell is a human cell. In some embodiments, the cell is transfected or transduced by the nucleic acid vector using a method selected from the group consisting of electroporation, sonoporation, biolistics (e.g., Gene Gun), lipid transfection, polymer transfection, nanoparticles, viral transfection (e.g., retrovirus, lentivirus, AAV) or polyplexes.

In some embodiments, the engineered immune cells expressing at their cell surface membrane an antigen-specific CAR comprise a percentage of stem cell memory and central memory cells greater than 10%, 20%, 30%, 40%, 50%, 60%, 70%, 80%, 90%, or 100%.

In some embodiments, engineered immune cells expressing at their cell surface membrane an antigen-specific CAR comprise a percentage of stem cell memory and central memory cells of about 10% to about 60%, about 10% to about 50%, about 10% to about 40%, about 15% to about 50%, about 15% to about 40%, about 20% to about 60%, or about 20% to about 70%.

In some embodiments, engineered immune cells expressing at their cell surface membrane an antigen-specific CAR enriched in $T_{CM}$ and/or $T_{SCM}$ cells such that the engineered immune cells comprise at least about 60%, 65%, 70%, 75%, or 80% combined $T_{CM}$ and $T_{SCM}$ cells. In some embodiments, engineered immune cells expressing at their cell surface membrane an antigen-specific CAR are enriched in $T_{CM}$ and/or $T_{SCM}$ cells such that the engineered immune cells comprise at least about 70% combined $T_{CM}$ and $T_{SCM}$ cells. In some embodiments, engineered immune cells expressing at their cell surface membrane an antigen-specific CAR e enriched in $T_{CM}$ and/or $T_{SCM}$ cells such that the engineered immune cells comprise at least about 75% combined $T_{CM}$ and/or $T_{SCM}$ cells.

In some embodiments, an engineered immune cell is an inflammatory T-lymphocyte that expresses a CAR. In some embodiments, an engineered immune cell is a cytotoxic T-lymphocyte that expresses a CAR. In some embodiments, an engineered immune cell is a regulatory T-lymphocyte that expresses a CAR. In some embodiments, an engineered immune cell is a helper T-lymphocyte that expresses a CAR.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, cyclophosphamide, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production.

In some embodiments, isolated cells or cell lines of the disclosure can comprise a pTα or a functional variant thereof. In some embodiments, an isolated cell or cell line can be further genetically modified by disrupting or inactivating the TCRα gene.

The disclosure also provides engineered immune cells comprising any of the CAR polynucleotides described herein. In some embodiments, a CAR can be introduced into an immune cell as a transgene via a plasmid vector. In some embodiments, the plasmid vector can also contain, for example, a selection marker which provides for identification and/or selection of cells which received the vector.

CAR polypeptides can be synthesized in situ in the cell after introduction of polynucleotides encoding the CAR polypeptides into the cell. Alternatively, CAR polypeptides can be produced outside of cells, and then introduced into cells. Methods for introducing a polynucleotide construct into cells are known in the art. In some embodiments, stable transformation methods (e.g., using a lentiviral vector) can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides can be introduced into a cell by any suitable means such as for example, recombinant viral vectors (e.g., retroviruses, adenoviruses), liposomes, and the like. Transient transformation methods include, for example without limitation, microinjection, electroporation or particle bombardment. Polynucleotides can be included in vectors, such as for example plasmid vectors or viral vectors.

In some embodiments, isolated nucleic acids are provided comprising a promoter operably linked to a first polynucleotide encoding an antigen binding domain, at least one costimulatory molecule, and an activating domain. In some embodiments, the nucleic acid construct is contained within a viral vector. In some embodiments, the viral vector is selected from the group consisting of retroviral vectors, murine leukemia virus vectors, SFG vectors, adenoviral vectors, lentiviral vectors, adeno-associated virus (AAV) vectors, Herpes virus vectors, and vaccinia virus vectors. In some embodiments, the nucleic acid is contained within a plasmid.

In some embodiments, the isolated nucleic construct is contained within a viral vector and is introduced into the genome of an engineered immune cell by random integration, e.g., lentiviral- or retroviral-mediated random integration. In some embodiments, the isolated nucleic acid construct is contained in a viral vector or a non-viral vector and is introduced into the genome of an engineered immune cell by site-specific integration, e.g., adenovirus-mediated site-specific integration.

Manufacture of Engineered Immune Cells

A variety of known techniques can be utilized in making the polynucleotides, polypeptides, vectors, antigen binding domains, immune cells, compositions, and the like according to the disclosure.

Prior to the in vitro manipulation or genetic modification of the immune cells described herein, the cells can be obtained from a subject. Cells expressing a CAR can be derived from an allogeneic or autologous source and can be depleted of endogenous TCR as described herein.

a. Source Material

In some embodiments, the immune cells comprise T cells. T cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In some embodiments, T cells can be obtained from a volume of blood collected from the subject using any number of techniques known to the skilled person, such as FICOLL™ separation.

Cells can be obtained from the circulating blood of an individual by apheresis. The apheresis product typically contains lymphocytes, including T cells, monocytes, granulocytes, B cells, other nucleated white blood cells, red blood cells, and platelets. In some embodiments, the cells collected by apheresis can be washed to remove the plasma fraction, and then placed in an appropriate buffer or media for subsequent processing.

In some embodiments, T cells are isolated from PBMCs by lysing the red blood cells and depleting the monocytes, for example, using centrifugation through a PERCOLL™ gradient. A specific subpopulation of T cells, (e.g., CD28+, CD4+, CD45RA−, and CD45RO+T cells or CD28+, CD4+, CDS+, CD45RA−, CD45RO+, and CD62L+ T cells) can be further isolated by positive or negative selection techniques known in the art. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. Flow cytometry and cell sorting can also be used to isolate cell populations of interest for use in the present disclosure.

PBMCs can be used directly for genetic modification with the immune cells (such as CARs or TCRs) using methods as described herein. In certain embodiments, after isolating the PBMCs, T lymphocytes can be further isolated and both cytotoxic and helper T lymphocytes can be sorted into naive, memory, and effector T cell subpopulations either before or after genetic modification and/or expansion. In some embodiments, CD8+ cells are further sorted into naive, stem cell memory, central memory, and effector cells by identifying cell surface antigens that are associated with each of these types of CD8+ cells. In some embodiments, the expression of phenotypic markers of central memory T cells include CD27, CD45RA, CD45RO, CD62L, CCR7, CD28, CD3, and CD127 and are negative for granzyme B. In some embodiments, stem cell memory T cells are CD45RO−, CD62L+, CD8+ T cells. In some embodiments, central memory T cells are CD45RO+, CD62L+, CD8+ T cells. In some embodiments, effector T cells are negative for CD62L, CCR7, CD28, and CD127, and positive for granzyme B and perforin. In some embodiments, CD4+ T cells are further sorted into subpopulations. For example, CD4+ T helper cells can be sorted into naive, central memory, and effector cells by identifying cell populations that have cell surface antigens.

b. Stem Cell Derived Immune Cells

In some embodiments, the immune cells can be derived from embryonic stem (ES) or induced pluripotent stem (iPS) cells. Suitable HSCs, mesenchymal, iPS cells and other types of stem cells can be cultivated immortal cell lines or isolated directly from a patient. Various methods for isolating, developing, and/or cultivating stem cells are known in the art and can be used to practice the present disclosure.

In some embodiments, the immune cell is an induced pluripotent stem cell (iPSC) derived from a reprogrammed T-cell. In some embodiments, the source material can be an induced pluripotent stem cell (iPSC) derived from a T cell or a non-T cell. In some embodiments, the immune cell is an iPSC-derived T cell. In some embodiments, the immune cell is an iPSC-derived NK cells. The source material can be an embryonic stem cell. The source material can be a B cell, or any other cell from peripheral blood mononuclear cell isolates, hematopoietic progenitor, hematopoietic stem cell, mesenchymal stem cell, adipose stem cell, or any other somatic cell type.

c. Genetic Modification of isolated cells

The immune cells, such as T cells, can be genetically modified following isolation using known methods, or the immune cells can be activated and expanded (or differentiated in the case of progenitors) in vitro prior to being genetically modified. In some embodiments, the isolated immune cells are genetically modified to reduce or eliminate expression of endogenous TCRα and/or CD52. In some embodiments, the cells are genetically modified using gene editing technology (e.g., CRISPR/Cas9, CRISPR/Cas12a, a zinc finger nuclease (ZFN), a TALEN, a MegaTAL, a meganuclease) to reduce or eliminate expression of endogenous proteins (e.g., TCRα and/or CD52). In another embodiment, the immune cells, such as T cells, are genetically modified with the chimeric antigen receptors described herein (e.g., transduced with a viral vector comprising one or more nucleotide sequences encoding a CAR) and then are activated and/or expanded in vitro.

Certain methods for making the constructs and engineered immune cells of the disclosure are described in PCT application PCT/US15/14520, the contents of which are hereby incorporated by reference in their entirety.

It will be appreciated that PBMCs can further include other cytotoxic lymphocytes such as NK cells or NKT cells. An expression vector carrying the coding sequence of a chimeric receptor as disclosed herein can be introduced into a population of human donor T cells, NK cells or NKT cells. Successfully transduced T cells that carry the expression vector can be sorted using flow cytometry to isolate CD3 positive T cells and then further propagated to increase the number of these CAR expressing T cells in addition to cell activation using anti-CD3 antibodies and IL-2 or other methods known in the art as described elsewhere herein. Standard procedures are used for cryopreservation of T cells expressing the CAR for storage and/or preparation for use in a human subject. In one embodiment, the in vitro transduction, culture and/or expansion of T cells are performed in the absence of non-human animal derived products such as fetal calf serum and fetal bovine serum.

For cloning of polynucleotides, the vector can be introduced into a host cell (an isolated host cell) to allow replication of the vector itself and thereby amplify the copies of the polynucleotide contained therein. The cloning vectors can contain sequence components generally include, without limitation, an origin of replication, promoter sequences, transcription initiation sequences, enhancer sequences, and selectable markers. These elements can be selected as appropriate by a person of ordinary skill in the art. For example, the origin of replication can be selected to promote autonomous replication of the vector in the host cell.

In some embodiments, the present disclosure provides isolated host cells containing the vector provided herein. The host cells containing the vector can be useful in expression or cloning of the polynucleotide contained in the vector. Suitable host cells can include, without limitation, prokaryotic cells, fungal cells, yeast cells, or higher eukaryotic cells such as mammalian cells, particularly human cells.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In a further embodiment, a mixture of different expression vectors can be used in genetically modifying a donor population of immune effector cells wherein each vector encodes a different CAR as disclosed herein. The resulting transduced immune effector cells form a mixed population of engineered cells, with a proportion of the engineered cells expressing more than one different CARs.

In one embodiment, the disclosure provides a method of storing genetically engineered cells expressing CARs or TCRs. This involves cryopreserving the immune cells such that the cells remain viable upon thawing. A fraction of the immune cells expressing the CARs can be cryopreserved by methods known in the art to provide a permanent source of such cells for the future treatment of patients afflicted with a malignancy. When needed, the cryopreserved transformed immune cells can be thawed, grown and expanded for more such cells.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

d. Allogeneic CAR T cells

The process for manufacturing allogeneic CAR T therapy involves harvesting healthy, selected, screened and tested T cells from healthy donors. Next, the T cells are engineered to express CARs, which recognize certain cell surface proteins that are expressed in hematologic or solid tumors. Allogeneic T cells are gene editing to reduce the risk of graft versus host disease (GvHD) and to prevent allogeneic rejection. A T cell receptor gene (e.g., TCRα, TCRβ) is knocked out to avoid GvHD. The CD52 gene can be knocked out to render the CAR T product resistant to anti-CD52 antibody treatment. Anti-CD52 antibody treatment can therefore be used to suppress the host immune system and allow the CAR T to stay engrafted to achieve full therapeutic impact. The engineered T cells then undergo a purification step and are ultimately cryopreserved in vials for delivery to patients.

e. Autologous CAR T Cells

Autologous chimeric antigen receptor (CAR) T cell therapy, involves collecting a patient's own cells (e.g., white blood cells, including T cells) and genetically engineering the T cells to express CARs that recognize target expressed on the cell surface of one or more specific cancer cells and kill cancer cells. The engineered cells are then cryopreserved and subsequently administered to the patient.

Pharmaceutical Composition

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

In embodiments, desired treatment amounts of cells in the composition are generally at least 2 cells (for example, at least 1 CD8+ central or stem cell memory T cell and at least 1 CD4+ helper T cell subset; or two or more CD8+ central or stem cell memory T cell; or two or more CD4+ helper T cell subset) or is more typically greater than $10^2$ cells, and up to and including $10^6$, up to and including $10^7$, $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present disclosure, particularly since all the infused cells will be redirected to a particular target antigen, lower numbers of cells, in the range of about $10^5$/kilogram or about $10^6$/kilogram ($10^6$-$10^{11}$ per patient) can be administered. CAR treatments can be administered multiple times at dosages within these ranges. The cells can be autologous, allogeneic, or heterologous to the patient undergoing therapy.

The CAR expressing cell populations of the present disclosure can be administered either alone, or as a pharmaceutical composition in combination with diluents and/or with other components such as IL-2 or other cytokines or cell populations. Pharmaceutical compositions of the present disclosure can comprise a CAR or TCR expressing cell population, such as T cells, as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

The pharmaceutical compositions (solutions, suspensions or the like), can include one or more of the following: sterile diluents such as water for injection, saline solution, preferably physiological saline, Ringer's solution, isotonic sodium chloride, fixed oils such as synthetic mono- or diglycerides which can serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic. An injectable pharmaceutical composition is preferably sterile.

Methods of Treatment

The disclosure comprises methods for treating or preventing a disease (e.g., cancer) in a patient, comprising administering to a patient in need thereof an effective amount of CAR T cells, or engineered immune cells comprising a CAR disclosed herein. In some embodiments, the effective amount of CAR T cells or engineered immune cells have been analyzed for various attributes according to the methods described in the instant disclosure. In some embodiments, the CAR T cell drug product for therapeutic use has been analyzed for various attributes, such as potency or polyfunctionality according to the methods described in the instant disclosure. In some embodiments, the CAR T cells are TCR-CAR T cells, and the CAR T drug product for therapeutic use has been analyzed for various attributes, such as the amount or percentage of remaining TCR+ CAR T cells and/or potency or polyfunctionality according to the methods described in the instant disclosure.

Methods are provided for treating diseases or disorders, including cancer. In some embodiments, the disclosure relates to creating a T cell-mediated immune response in a subject, comprising administering an effective amount of the engineered immune cells of the present application to the subject. In some embodiments, the T cell-mediated immune response is directed against a target cell or cells. In some embodiments, the engineered immune cell comprises a chimeric antigen receptor (CAR). In some embodiments, the target cell is a tumor cell. In some aspects, the disclosure comprises a method for treating or preventing a malignancy, said method comprising administering to a subject in need thereof an effective amount of at least one isolated antigen binding domain described herein. In some aspects, the disclosure comprises a method for treating or preventing a malignancy, said method comprising administering to a subject in need thereof an effective amount of at least one immune cell, wherein the immune cell comprises at least one chimeric antigen receptor, T cell receptor, and/or isolated antigen binding domain as described herein. The CAR containing immune cells of the disclosure can be used to treat malignancies involving aberrant expression of biomarkers. In some embodiments, CAR containing immune cells of the disclosure can be used to treat small cell lung cancer, melanoma, low grade gliomas, glioblastoma, medullary thyroid cancer, carcinoids, dispersed neuroendocrine tumors in the pancreas, bladder and prostate, testicular cancer, and lung adenocarcinomas with neuroendocrine features. In exemplary embodiments, the CAR containing immune cells, e.g., CAR-T cells of the disclosure are used to treat small cell lung cancer.

Also provided are methods for reducing the size of a tumor in a subject, comprising administering to the subject an engineered cell of the present disclosure to the subject, wherein the cell comprises a chimeric antigen receptor comprising an antigen binding domain and binds to an antigen on the tumor.

In some embodiments, the subject has a solid tumor, or a blood malignancy such as lymphoma or leukemia. In some embodiments, the engineered cell is delivered to a tumor bed. In some embodiments, the cancer is present in the bone marrow of the subject. In some embodiments, the engineered cells are autologous immune cells, e.g., autologous T cells. In some embodiments, the engineered cells are allogeneic immune cells, e.g., allogeneic T cells. In some embodiments, the engineered cells are heterologous immune cells, e.g., heterologous T cells. In some embodiments, the engineered cells of the present application are transfected or transduced in vivo. In other embodiments, the engineered cells are transfected or transduced ex vivo. As used herein, the term "in vitro cell" refers to any cell which is cultured ex vivo.

A "therapeutically effective amount," "effective dose," "effective amount," or "therapeutically effective dosage" of a therapeutic agent, e.g., engineered CART cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Desired treatment amounts of cells in the composition is generally at least 2 cells (for example, at least 1 CD8+ central memory T cell and at least 1 CD4+ helper T cell subset) or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present disclosure, particularly since all the infused cells will be redirected to a particular target antigen, lower numbers of cells, in the range of $10^6$/kilogram ($10^6$-$10^{11}$ per patient) can be administered. CAR treatments can be administered multiple times at dosages within these ranges. The cells can be autologous, allogeneic, or heterologous to the patient undergoing therapy.

In some embodiments, the therapeutically effective amount of the CAR T cells is about $1\times10^5$ cells/kg, about $2\times10^5$ cells/kg, about $3\times10^5$ cells/kg, about $4\times10^5$ cells/kg, about $5\times10^5$ cells/kg, about $6\times10^5$ cells/kg, about $7\times10^5$ cells/kg, about $8\times10^5$ cells/kg, about $9\times10^5$ cells/kg, $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, target doses for CAR+/CAR-T+/TCR+ cells range from $1\times10^6$-$2\times10^8$ cells/kg, for example $2\times10^6$ cells/kg. It will be appreciated that doses above and below this range can be appropriate for certain subjects, and appropriate dose levels can be determined by the healthcare provider as needed. Additionally, multiple doses of cells can be provided in accordance with the disclosure.

In some aspect, the disclosure comprises a pharmaceutical composition comprising at least one antigen binding domain as described herein and a pharmaceutically acceptable excipient. In some embodiments, the pharmaceutical composition further comprises an additional active agent.

The CAR expressing cell populations of the present disclosure can be administered either alone, or as a pharmaceutical composition in combination with diluents and/or with other components such as IL-2 or other cytokines or cell populations. Pharmaceutical compositions of the present disclosure can comprise a CAR or TCR expressing cell population, such as T cells, as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

The pharmaceutical compositions (solutions, suspensions or the like), can include one or more of the following: sterile diluents such as water for injection, saline solution, preferably physiological saline, Ringer's solution, isotonic sodium chloride, fixed oils such as synthetic mono- or diglycerides which can serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic. An injectable pharmaceutical composition is preferably sterile.

In some embodiments, upon administration to a patient, engineered immune cells expressing at their cell surface any one of the antigen-specific CARs described herein can reduce, kill or lyse endogenous antigen-expressing cells of the patient. In one embodiment, a percentage reduction or lysis of antigen-expressing endogenous cells or cells of a cell line expressing an antigen by engineered immune cells expressing any one of an antigen-specific CARs described herein is at least about or greater than 10%, 15%, 20%, 25%, 30%, 35%, 40%, 45%, 50%, 55%, 60%, 65%, 70%, 75%, 80%, 85%, 90%, or 95%. In one embodiment, a percentage reduction or lysis of antigen-expressing endogenous cells or cells of a cell line expressing an antigen by engineered immune cells expressing antigen-specific CARs is about 5% to about 95%, about 10% to about 95%, about 10% to about 90%, about 10% to about 80%, about 10% to about 70%, about 10% to about 60%, about 10% to about 50%, about 10% to about 40%, about 20% to about 90%, about 20% to about 80%, about 20% to about 70%, about 20% to about 60%, about 20% to about 50%, about 25% to about 75%, or about 25% to about 60%. In one embodiment, the endogenous antigen-expressing cells are endogenous antigen-expressing bone marrow cells.

In one embodiment, the percent reduction or lysis of target cells, e.g., a cell line expressing an antigen, by engineered immune cells expressing at their cell surface membrane an antigen-specific CAR of the disclosure can be measured using the assay disclosed herein.

The methods can further comprise administering one or more chemotherapeutic agent. In some embodiments, the chemotherapeutic agent is a lymphodepleting (preconditioning) chemotherapeutic. For example, methods of conditioning a patient in need of a T cell therapy comprising administering to the patient specified beneficial doses of cyclophosphamide (between 200 mg/m$^2$/day and 2000 mg/m$^2$/day, about 100 mg/m$^2$/day and about 2000 mg/m$^2$/day; e.g., about 100 mg/m$^2$/day, about 200 mg/m$^2$/day, about 300 mg/m$^2$/day, about 400 mg/m$^2$/day, about 500 mg/m$^2$/day, about 600 mg/m$^2$/day, about 700 mg/m$^2$/day, about 800 mg/m$^2$/day, about 900 mg/m$^2$/day, about 1000 mg/m$^2$/day, about 1500 mg/m$^2$/day or about 2000 mg/m$^2$/day) and specified doses of fludarabine (between 20 mg/m$^2$/day and 900 mg/m$^2$/day, between about 10 mg/m$^2$/day and about 900 mg/m$^2$/day; e.g., about 10 mg/m$^2$/day, about 20 mg/m$^2$/day, about 30 mg/m$^2$/day, about 40 mg/m$^2$/day, about 40 mg/m$^2$/day, about 50 mg/m$^2$/day, about 60 mg/m$^2$/day, about 70 mg/m$^2$/day, about 80 mg/m$^2$/day, about 90 mg/m$^2$/day, about 100 mg/m$^2$/day, about 500 mg/m$^2$/day or about 900 mg/m$^2$/day). A preferred dose regimen involves treating a patient comprising administering daily to the patient about 300 mg/m$^2$/day of cyclophosphamide and about 30 mg/m$^2$/day of fludarabine for three days prior to administration of a therapeutically effective amount of engineered T cells to the patient.

In some embodiments, lymphodepletion further comprises administration of a CD52 antibody. In some embodiments, the CD52 antibody is alemtuzumab. In some embodiments, the CD52 antibody is administered at a dose of about 13 mg/day IV.

In other embodiments, the antigen binding domain, transduced (or otherwise engineered) cells and the chemotherapeutic agent are administered each in an amount effective to treat the disease or condition in the subject.

In some embodiments, compositions comprising CAR-expressing immune effector cells disclosed herein can be administered in conjunction with any number of chemotherapeutic agents, which can be administered in any order. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RF S2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4 (5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell, polypeptide, or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell, polypeptide, or nucleic acid. In other embodiments, the chemotherapeutic agent is administered at least 1 month before administering the cell, polypeptide, or nucleic acid. In some embodiments, the methods further comprise administering two or more chemotherapeutic agents.

A variety of additional therapeutic agents can be used in conjunction with the compositions described herein. For example, potentially useful additional therapeutic agents include PD-1 inhibitors such as nivolumab (Opdivo®), pembrolizumab (Keytruda®), pembrolizumab, pidilizumab, and atezolizumab (Tcentriq®).

Additional therapeutic agents suitable for use in combination with the disclosure include, but are not limited to, ibrutinib (Imbruvica®), ofatumumab (Arzerra®), rituximab (Rituxan®), bevacizumab (Avastin®), trastuzumab (Herceptin®), trastuzumab emtansine (KADCYLA®, imatinib (Gleevec®), cetuximab (Erbitux®, panitumumab) (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR-containing immune cells can be administered with a therapeutic regimen to prevent cytokine release syndrome (CRS) or neurotoxicity. The therapeutic regimen to prevent cytokine release syndrome (CRS) or neurotoxicity can include lenzilumab, tocilizumab, atrial natriuretic peptide (ANP), anakinra, iNOS inhibitors (e.g., L-NIL or 1400W). In additional embodiments, the composition comprising CAR-containing immune cells can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF(GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, IL-21 a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

The following examples are offered for illustrative purposes only. Indeed, various modifications of the invention in addition to those shown and described herein will become apparent to those skilled in the art from the foregoing description.

EXAMPLES

Example 1 Identify Factors Affecting Drug Product Quality

The general consensus in the field was to complete drug product processing within as short a time window as possible to minimize the exposure time of formulated cells to cryopreservative containing formulation and other stress conditions. The time limit adds constraints to the manufacturing process, especially for allogeneic CAR T drug products, where the manufacturing process is designed to produce large number of doses per batch and thus may require longer drug product processing time.

We conducted process development studies to identify factors that can impact CAR T cells during the drug product process. FIG. 1 shows an exemplary workflow from harvesting cells to filling the drug product to freezing the drug product. Briefly, the engineered cells, such as CAR T cells, were resuspended in non-DMSO containing basal medium. The cell suspension was mixed with equal volume of DMSO-containing formulation to a final concentration of DMSO to 5% before the filling process was to begin. The data presented below were obtained from using exemplary CD19 CAR T cells.

Pre-freeze formulated CD19 CAR T cells were mixed during the filling process to keep the cells in suspension and ensure product homogeneity and dose content uniformity. Mixing of cells was done using Erlenmeyer flasks on a orbital shaker unless indicated otherwise. The mixing rate depended on the volume of formulation in the flask, ranging from 85 rpm to 140 rpm. The speed at the lower range was adopted for the following experiments in shaker flask mixing to ensure sufficient mixing while minimizing impacts on cell viability.

Figure 2B:
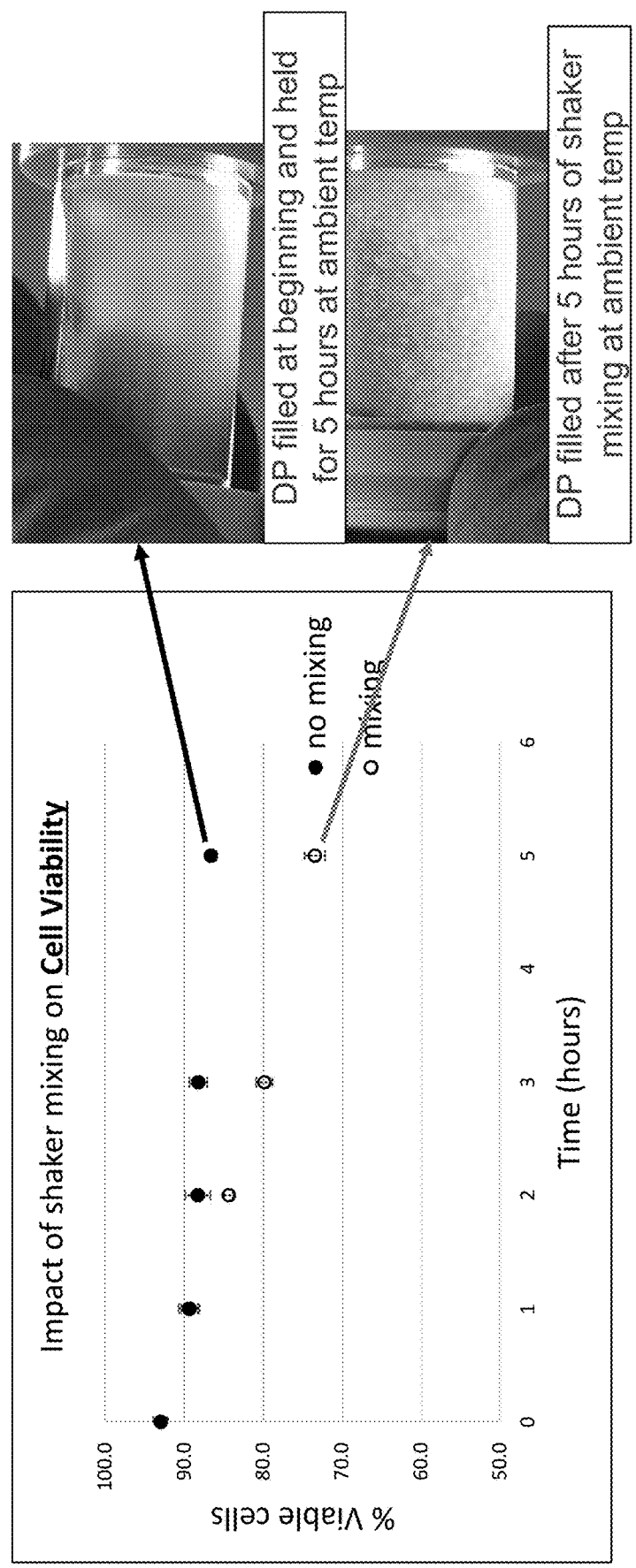

The viable cell density (VCD) and cell viability was measured using a fluorescent dye-based method and cell imager NucleoCounter® NC-200™ to determine the impact of mixing on cells. NucleoCounter® was used to count cells by detecting nuclei using two fluorescent dyes pre-loaded in the Vial-Cassette™: Acridine Orange (AO) stains all cells green while DAPI (4',6-diamidino-2-phenylindole) stains dead cells blue. Viable cell density (VCD) was calculated as (total cells−dead cells)/ml, and % cell viability was calculated as (total cells−dead cells)/total cells×100. The orbital shaker mixing was found to impact VCD (FIG. 2A) and % viability of cells (FIG. 2B) as compared to the drug product filled at the beginning of the process and held at room temperature for 5 hours without any further mixing.

Figure 3A:
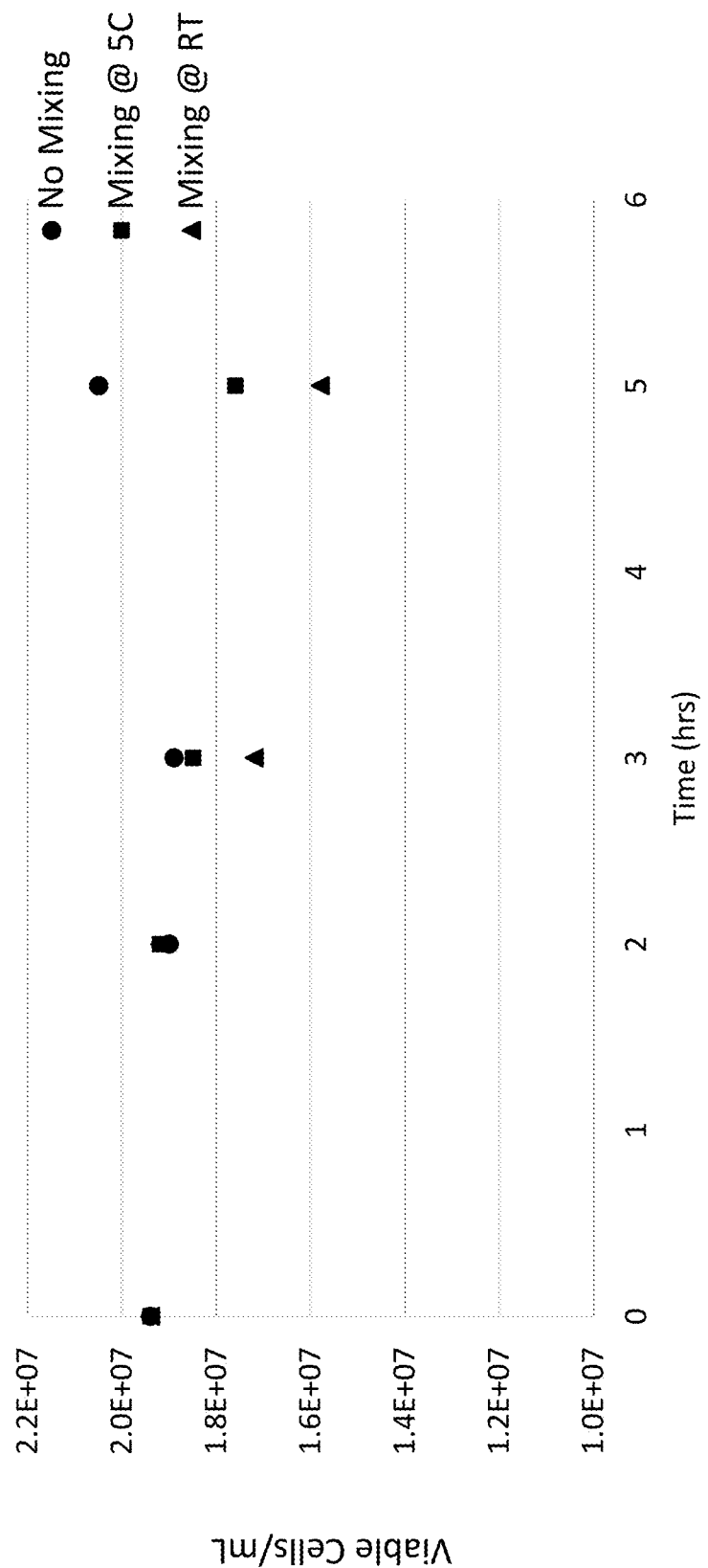
FIGS. 3A-3B show impact of orbital shaker mixing and formulation hold temperature on VCD and viability.
Figure 3B:
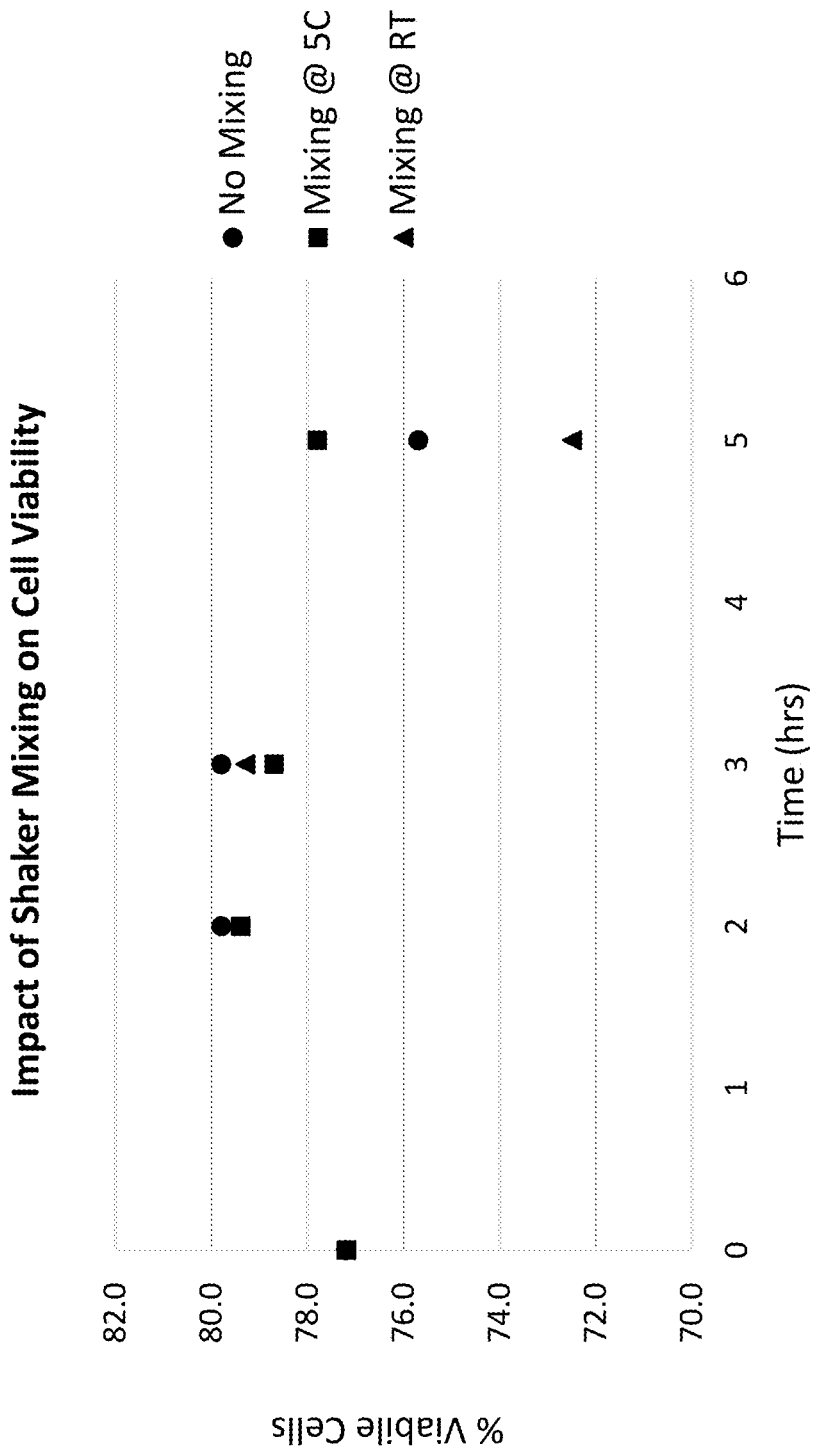

The impact of formulation hold temperature was also tested during shaker flask mixing. The data show that holding formulated cells at 5° C. during shaker flask mixing is better than holding the product at room temperature during shaker flask mixing when VCD and % cell viability were examined (FIGS. 3A and 3B, respectively).

Figure 4A:
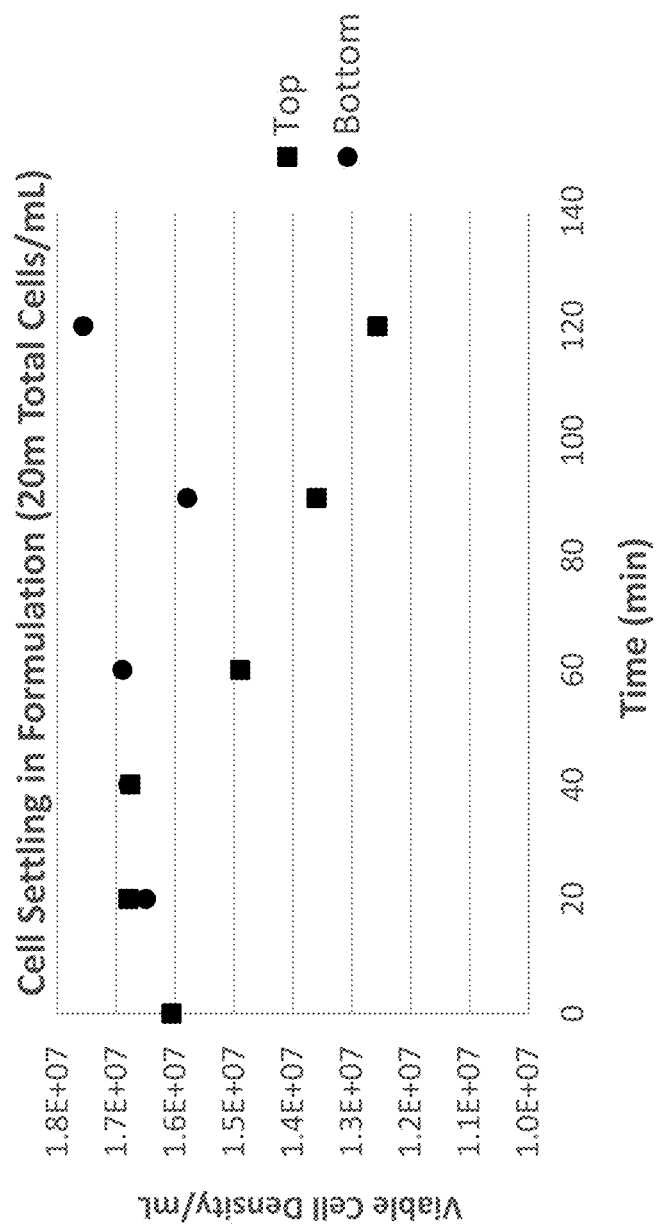
FIGS. 4A-4B show results of time course analysis of cell settling in a cell formulation containing 20E6/ml or 100E6/ml of CAR T cells.
Figure 4B:
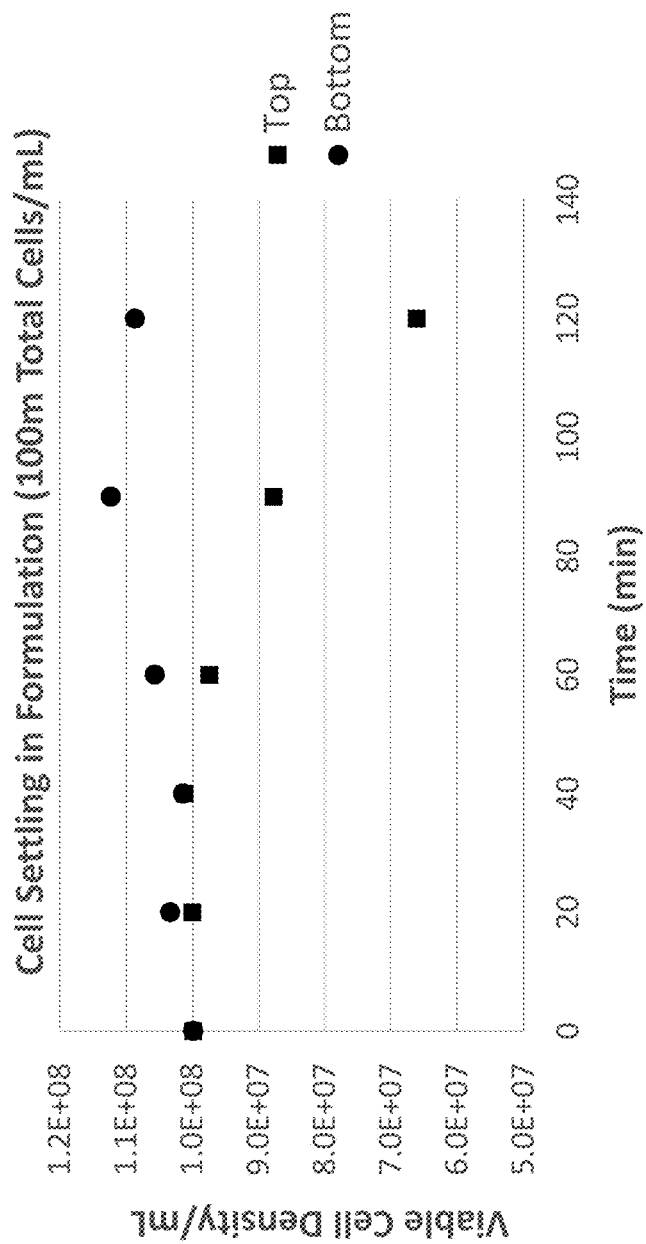

As part of the shaker flask mixing optimization, cell settling studies were done to evaluate the need for continuous mixing. Cell settling studies were done with cells formulated at 20E+06 viable cells/mL and 100E+06 viable cells/mL in Erlenmeyer flasks. The formulation in the flask was sampled at the top and bottom of the flask over a period of time without mixing. The results show that cell settling did not happen for at least 40 minutes for both cell concentrations tested (FIGS. 4A-4B).

The cell settling data indicate that the formulated cells do not need to be mixed continuously as the cells in the final formulation do not settle immediately. Without wishing to be bound by specific mechanisms, the delayed settling of cells could be due to the size of the cells and/or a higher viscosity of the final formulation. This finding led us to evaluate intermittent orbital shaker flask mixing. Additionally, a different type of mixing using a spinner flask and, e.g., a magnetic stir plate, was also evaluated. Both intermittent orbital shaker mixing (e.g., 2 minutes of mixing every 10 or 30 minutes at a speed of 85 rpm) and continuous spinner flask mixing of cells (e.g., 40 rpm) in final formulation showed better viable cell density (FIG. 5A) and % cell viability (FIG. 5B) over time as compared to continuous orbital shaker mixing at 85 rpm.

Figure 5A:
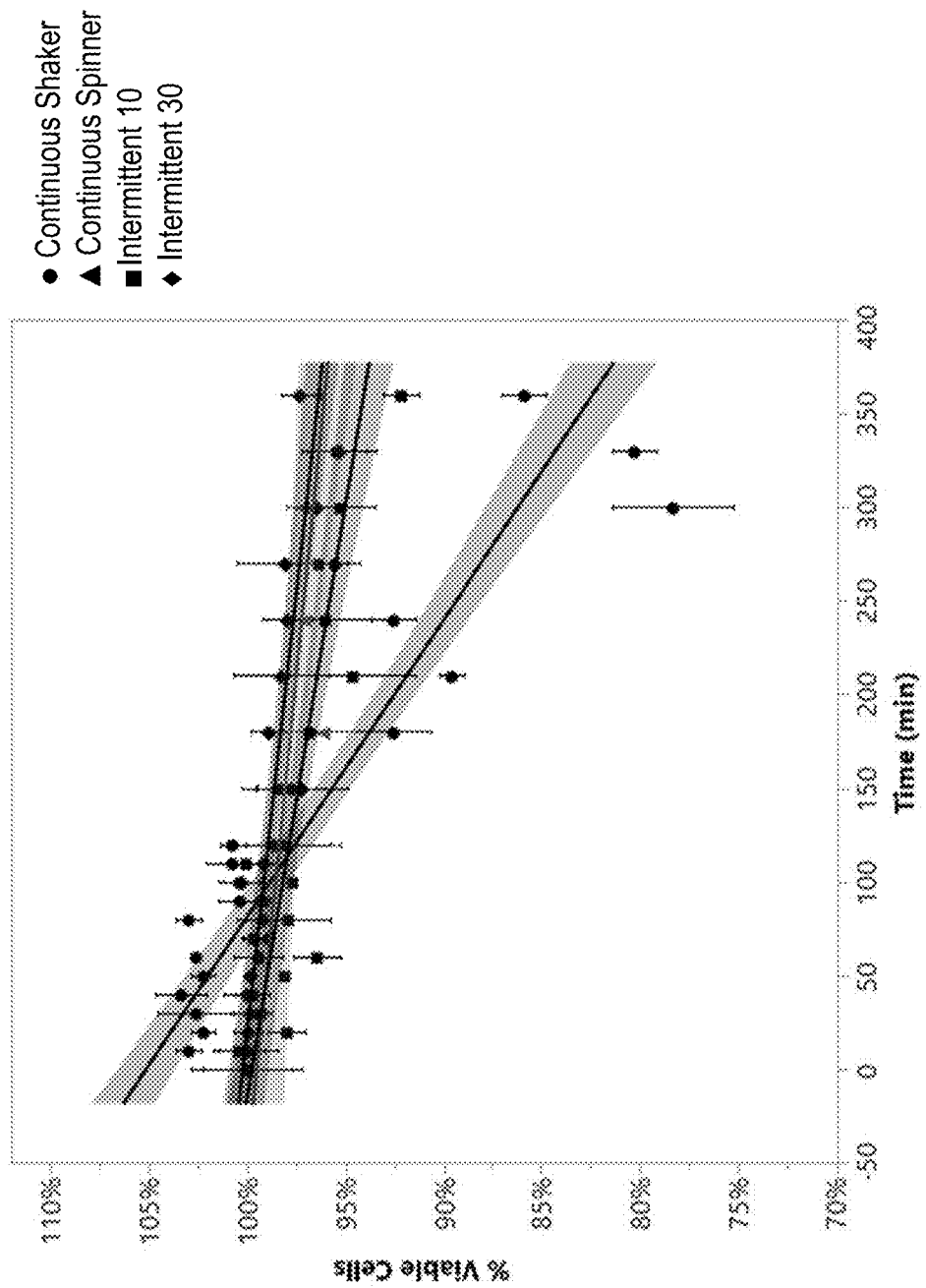
FIG. 5C compares results of VCD and viability of pre-freeze CAR T cell drug product after continuous mixing or intermittent mixing, both in a spinner flask. Continuous Shaker: formulated cells in Erlenmeyer shaker flasks on an orbital shaker platform in continuous mixing at 85 rpm; Continuous Spinner: formulated cells in spinner flasks on a magnetic stir plate in continuous mixing at 40 rpm; Int. Shaker 10: formulated cells in Erlenmeyer shaker flasks on an orbital shaker platform mixed at 85 rpm for 2 minutes every 10 minutes; Int. Shaker 30: formulated cells in Erlenmeyer shaker flasks on an orbital shaker platform mixed at 85 rpm for 2 minutes every 30 minutes; and Int. Spinner: formulated cells in spinner flasks on a magnetic stir plate mixed at 40 rpm for 2 minutes every 10 minutes. Triplets of samples were tested.
Figure 5B:
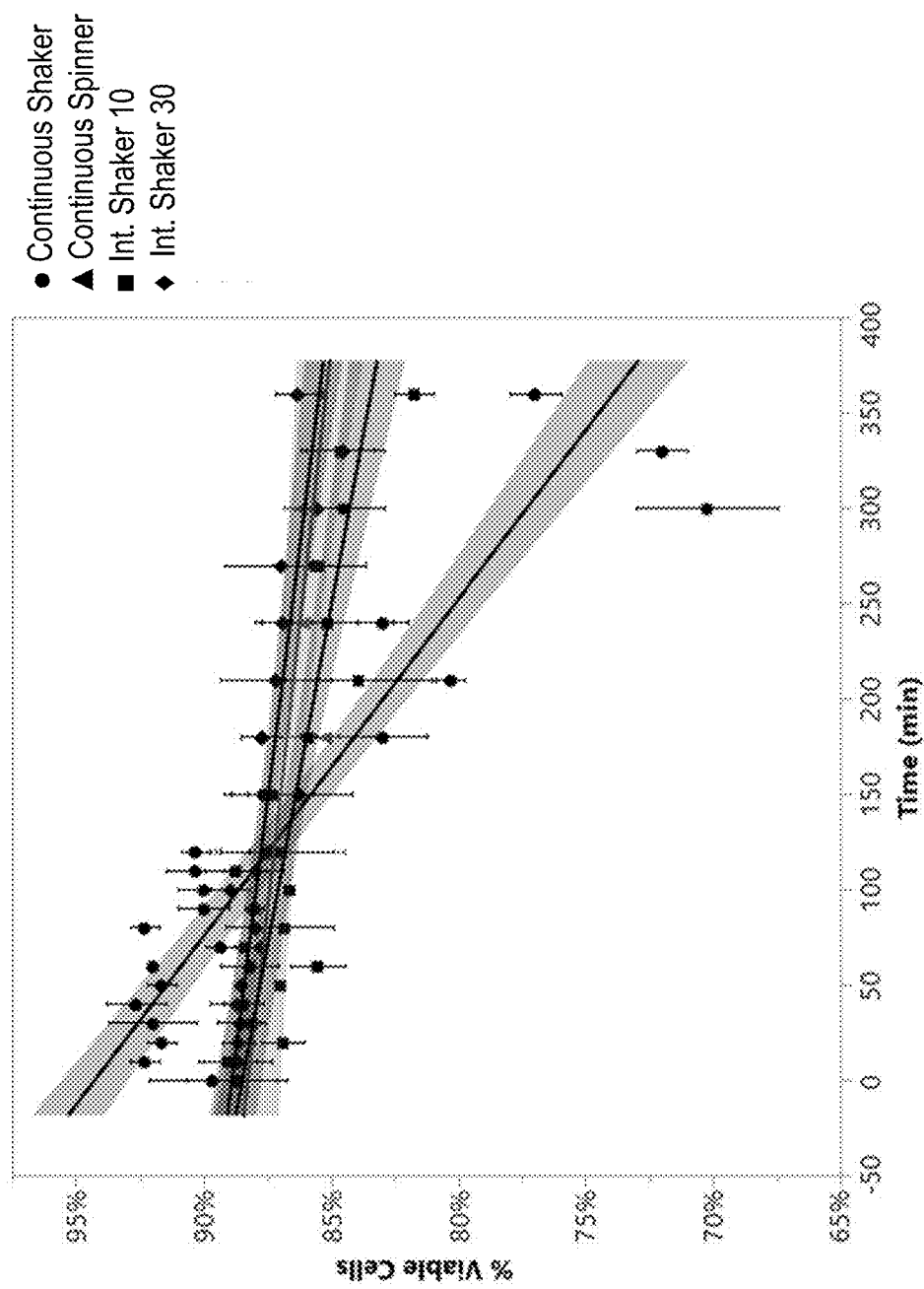

Shaker flask mixing is achieved by placing formulated cells in a shaker flask, such as an Erlenmeyer shaker flask, on e.g., an orbital shaking platform at a set speed. There are no moving parts within the flask, such as a paddle, which by making a direct contact with the cells in a flask may potentially damage the cells. On the other hand, a spinner flask that is equipped with, e.g., a top mounted paddle connected to a magnetic stir bar that comes in direct contact with the cells was thought to impact cells due to the shear force at the paddle. Thus, shaker flask mixing was presumed to generate less shear stress and be gentler to cells. But as shown in FIG. 5A and FIG. 5B, the VCD and % cell viability after continuous shaking in a spinner flask are both significantly better than those in continuous shaking in an orbital shaker flask. In addition, when the filling process was conducted using a shaker flask, the results from intermittent shaking are superior than continuous shaking.

Figure 5C:
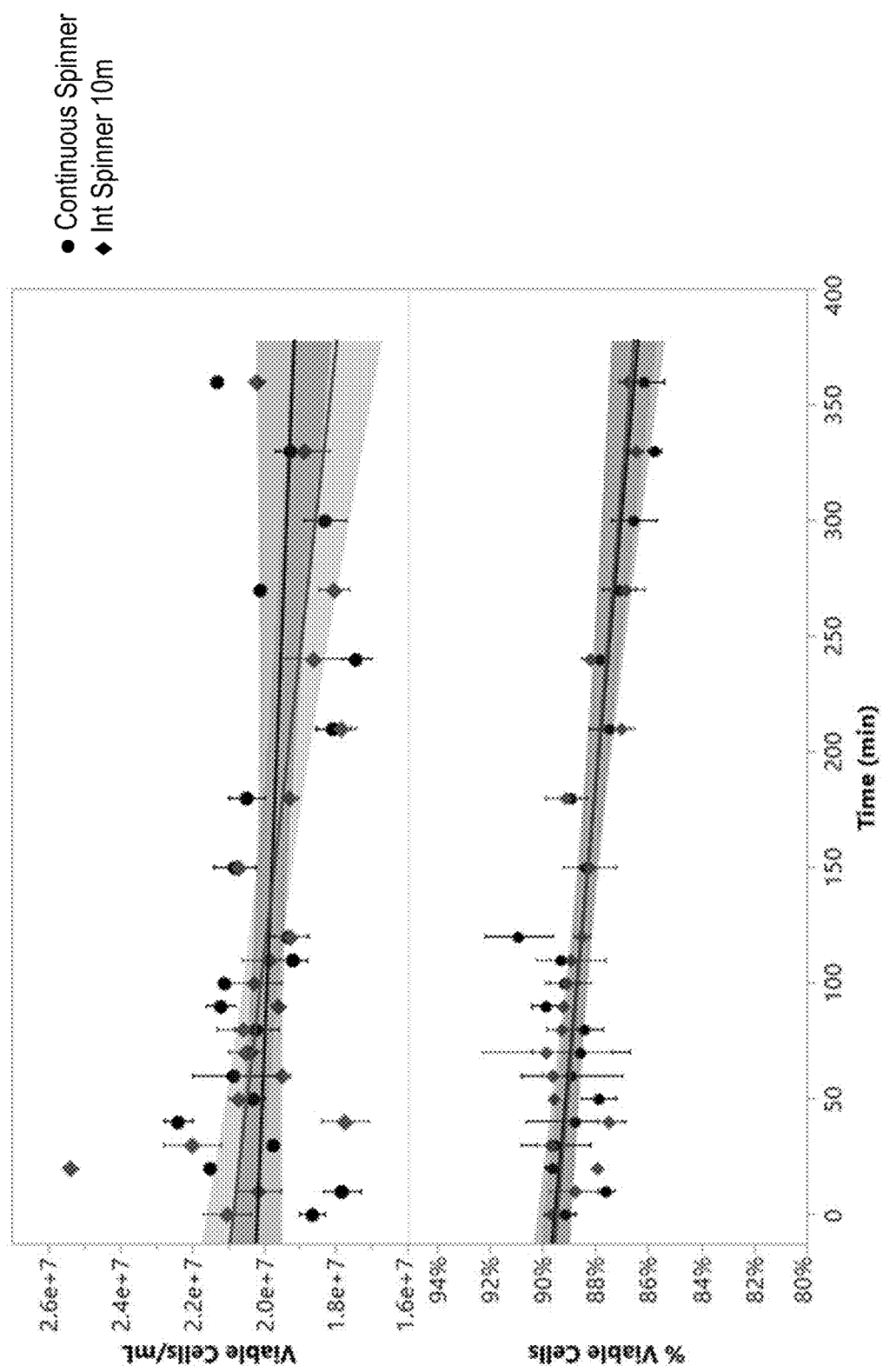

Next, intermittent shaking in a spinner flask (2 min of mixing at 40 rpm every 10 min) was further evaluated as compared with continuous mixing in a spinner flask (40 rpm). The results in FIG. 5C show that the results of intermittent mixing and continuous mixing in a spinner flask are comparable.

In summary, we unexpectedly found that it is not just the DMSO exposure time (as generally believed in the field) that may lead to cell damage during the drug product process, but other processing conditions (such as operating temperature, ways of mixing) also may have significant effects on cells. For example, a lower temperature can help improve cell viability compared to room temperature exposure during the filling process. Further, the data show that cell settling in the final formulation with 5% DMSO was a slow process. Thus, continuous mixing of cells during the filling process may not be required, in contrary to what was generally believed in the field. In addition to the time of mixing, it was also surprisingly found that the type of mixing employed during the filling process had a significant effect. The data presented here show that spinner flask mixing resulted in significantly higher viable cells as compared to continuous shaker flask mixing.

Example 2 Process Design to Increase Drug Product Filling Time Window

Figure 6:
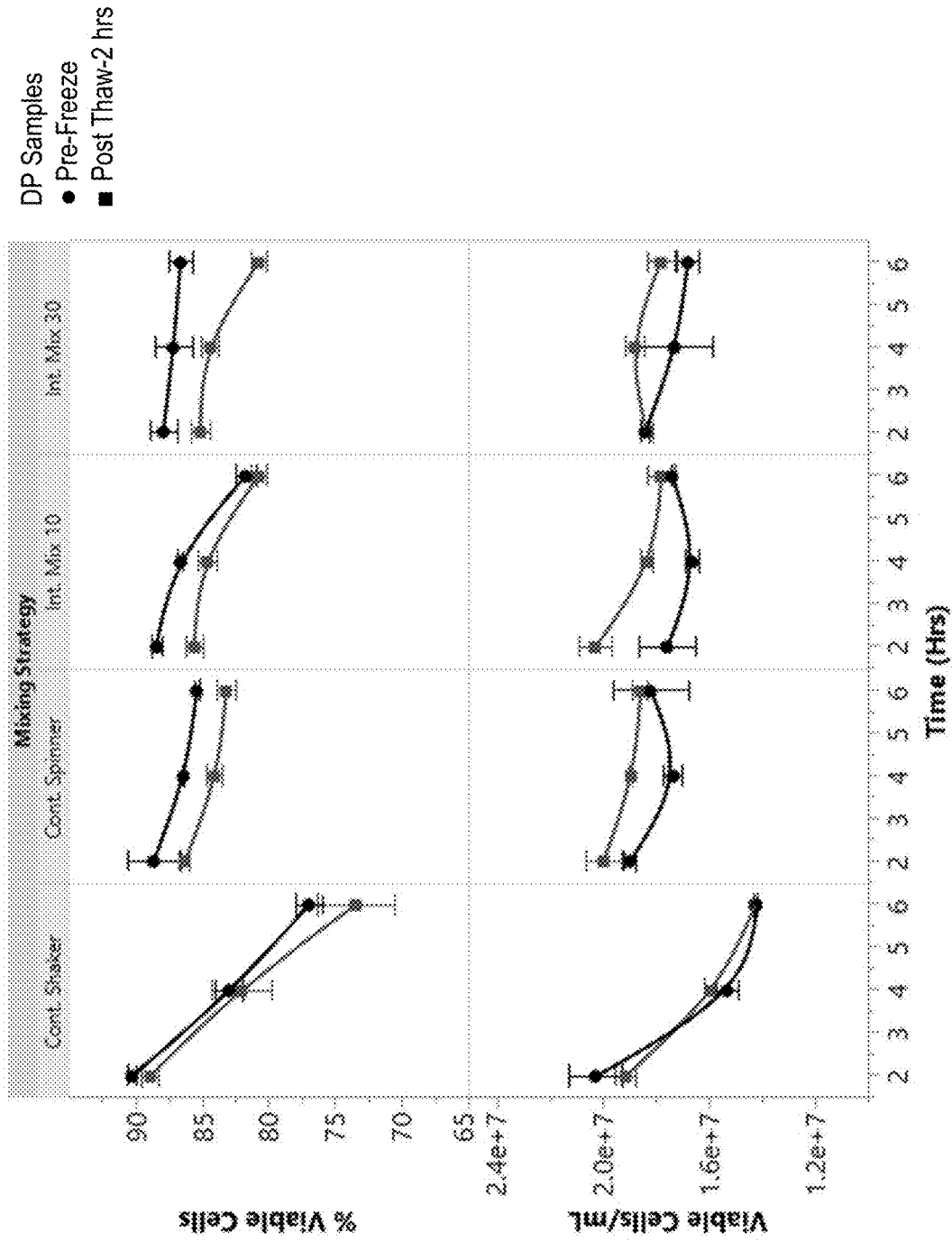
FIG. 6 shows results of VCD and % cell viability, as a function of fill time, of pre-freeze CAR T cells or post-thawed CAR T cells subjected to different filling processes. Triplets of samples were tested.

The above data suggest that it is feasible to increase fill-finish time window without negatively affecting cell viability. In the next experiment, we examined the VCD and % cell viability of pre-freeze CAR T cells under different mixing conditions during a 2-hour, 4-hour or 6-hour filling process (FIG. 6). Cells subjected to respective filling process were frozen down and any long term effects of the mixing process on post-thawed cells were also examined. An aliquot of frozen cells were thawed, subjected to a 2 hour hold at room temperature and the VCD and % cell viability were determined as shown in FIG. 6. The results in FIG. 6 show that continuous mixing in a spinner flask or intermittent mixing in a shaker flask performed better than continuous mixing in a shaker flask, using either pre-freeze or post-thaw drug products as examples. The VCD and viability were not significantly affected even past four hours during the filling process. In a separate experiment, post-thaw engineered CAR T cells were cultured for three days to confirm that the cells were viable and could recover and expand after the drug product process and freezing (data not shown).

Figure 7A:
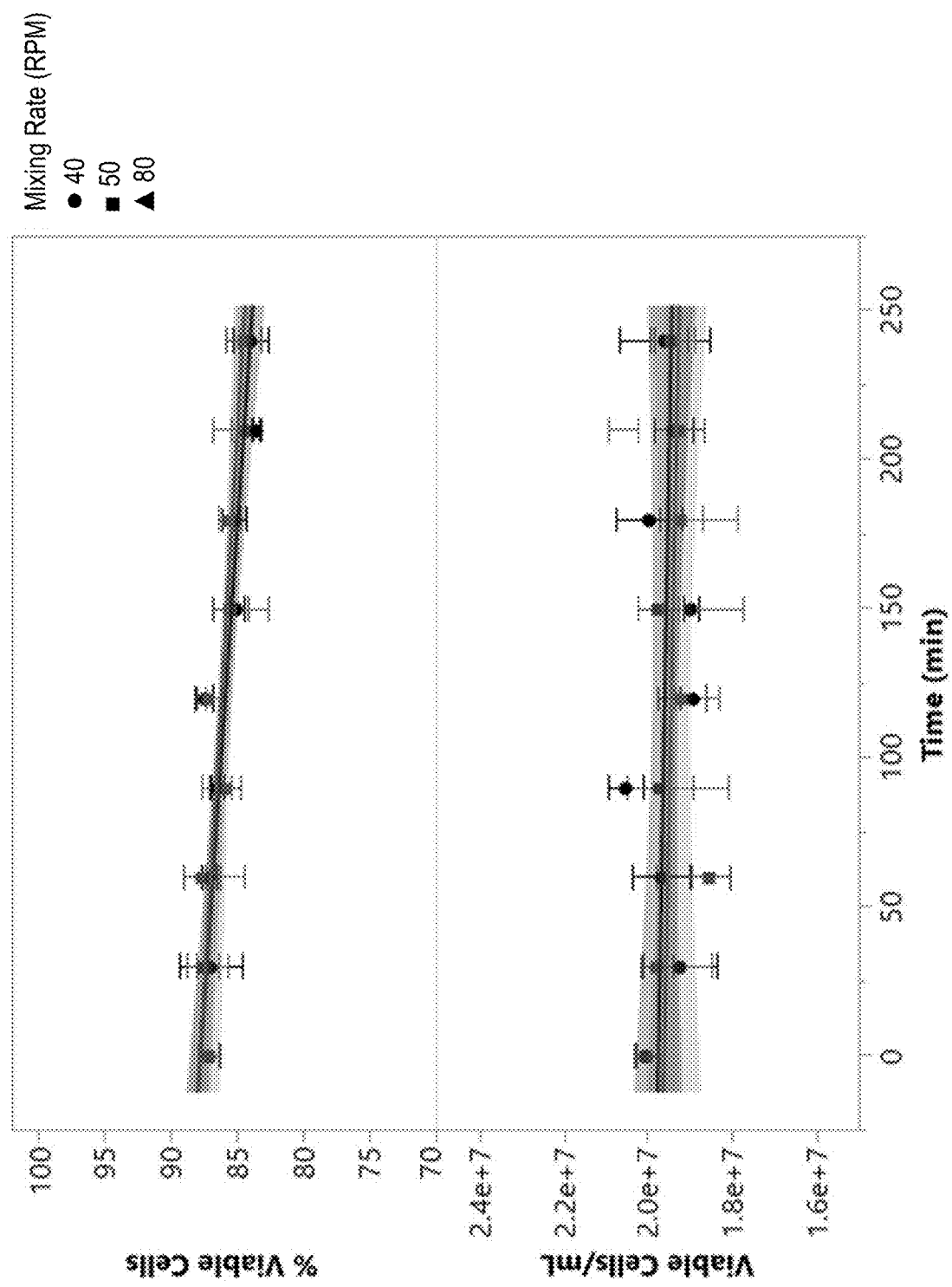
FIG. 7A shows VCD and % cell viability of CAR T cells in spinner flasks subjected to continuous mixing at different mixing rate.
Figure 7B:
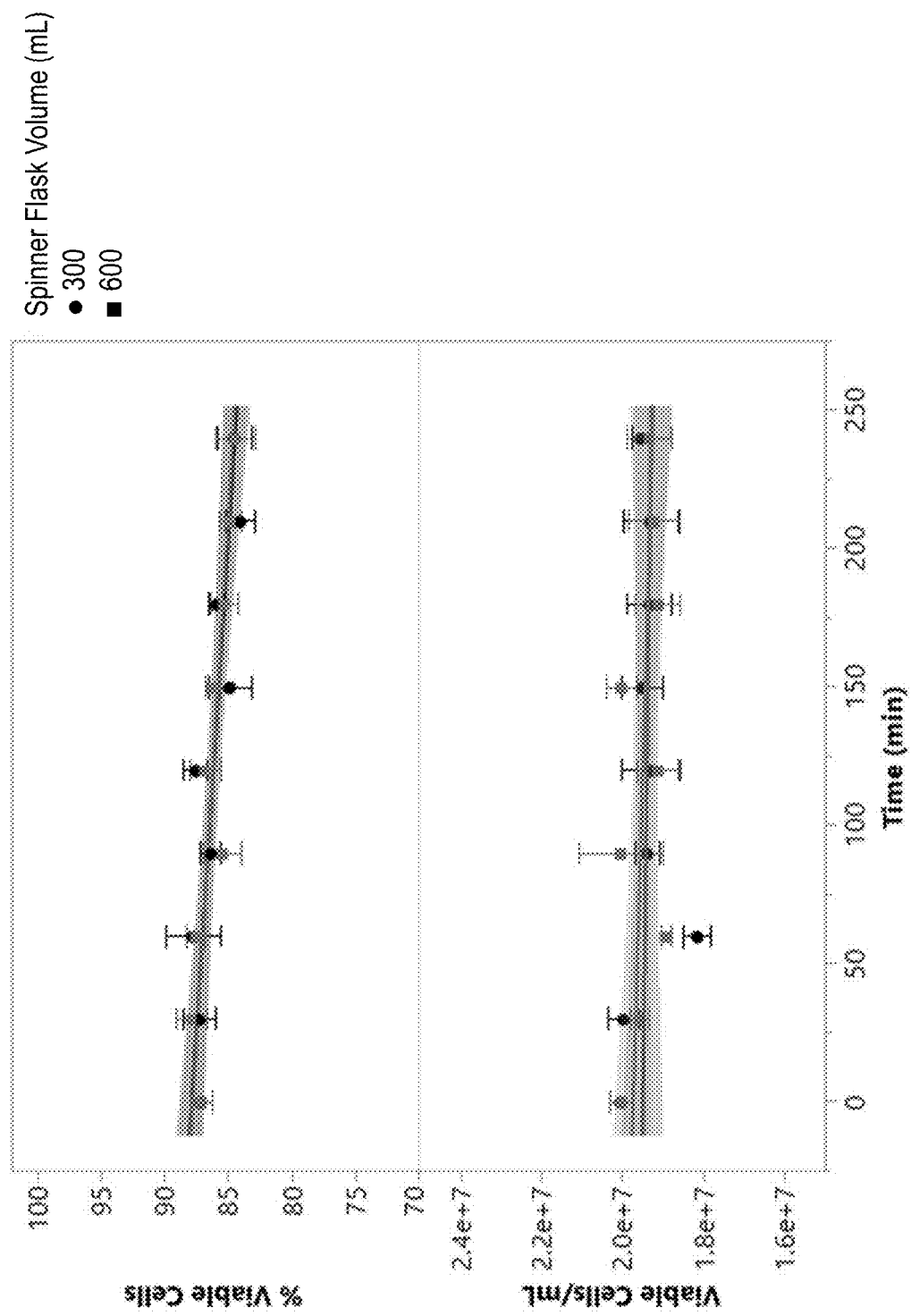
FIG. 7B shows VCD and % cell viability of CAR T cells in spinner flasks of starting volume of 300 ml or 600 ml subjected to continuous spinner flask mixing at 50 rpm. Triplets of samples were tested.

Although it was generally believed that shaker flask is gentler to cells in terms of shear stress, we unexpectedly found that spinner flask mixing outperformed shaker flask mixing in the filling process. We next examined the effects of mixing rate on pre-freeze drug product using spinner flask mixing. As shown in FIG. 7A, mix rate of 40-80 rpm in spinner flask mixing did not significantly impact the drug product in the course of four hours. We further examined whether the impact on cells mixed in a spinner flask is affected by the volume of the formulated cells. As shown in FIG. 7B, the VCD and % viability of a starting volume of 300 ml or 600 ml drug product subjected to continuous spinner flask mixing at 50 rpm are comparable in the course of four hours.

In summary, the data disclosed herein show that intermittent shaker flask mixing outperformed continuous shaker flask mixing. In addition, switching from shaker flasks to spinner flasks, either in continuous mixing or intermittent mixing, over a range of speed, showed improved VCD and cell viability as compared to continuous shaker flask mixing especially over extended period of time.

Example 3 Analysis of Product Quality

Figure 8A:
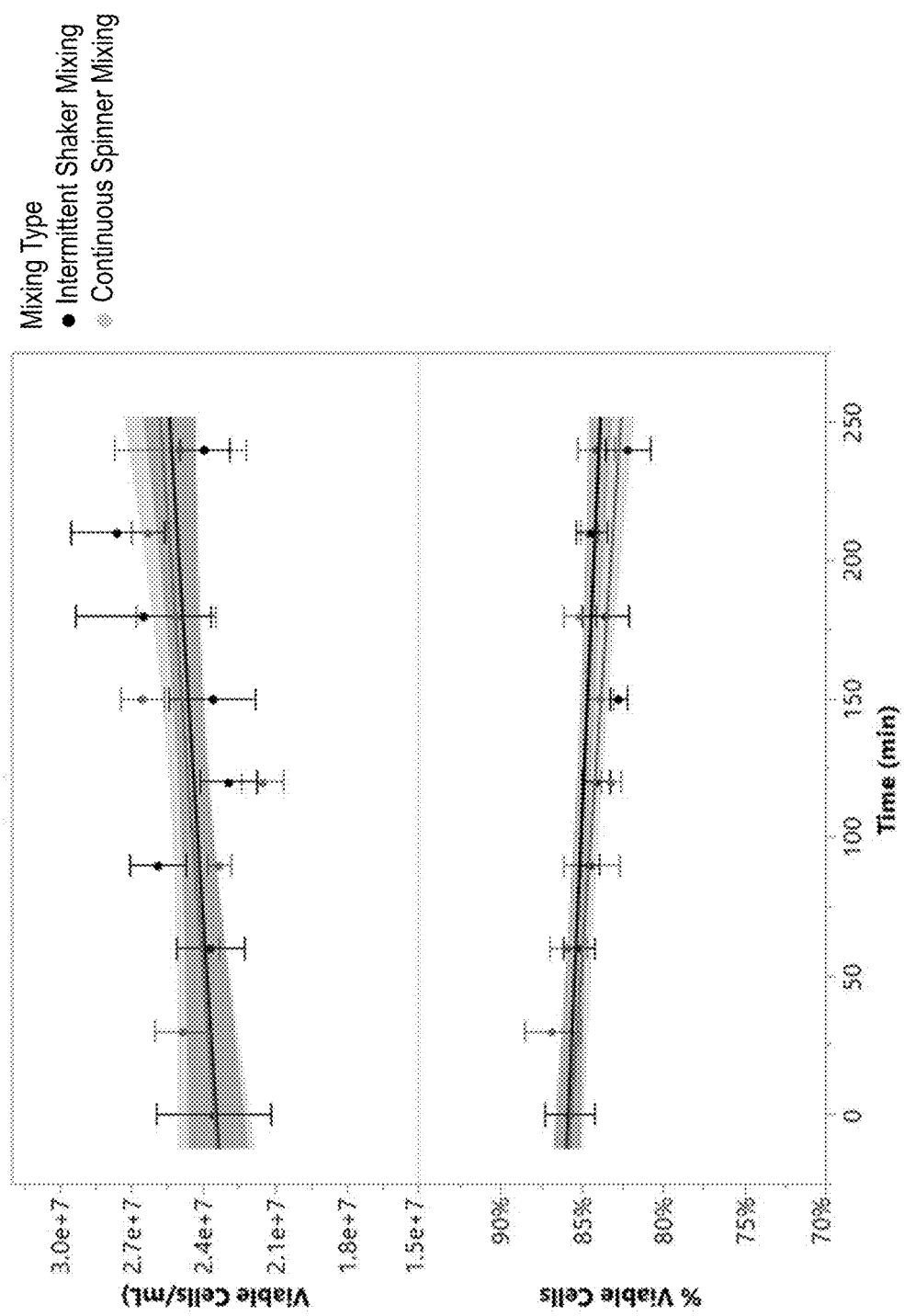
FIG. 8A compares the results of continuous mixing in spinner flasks and intermittent mixing in shaker flasks in the course of four hours of pre-freeze CAR T cells.

After the drug product process, the filled vials or containers were frozen for storage. We next analyzed post thawed drug product that had been processed by different mixing/filling processes to determine whether the post thawed formulated cells maintain viability. The data in FIG. 8A show that continuous mixing in a spinner flask at 40 rpm or intermittent mixing in a shaker flask for 2 min at 85 rpm every 30 min produced comparable results and neither significantly affected the VCD or % viability of pre-freeze drug product, in the course of four hours. The filled samples were frozen for storage for two or four hours, before the cells were thawed for further testing.

Figure 8B:
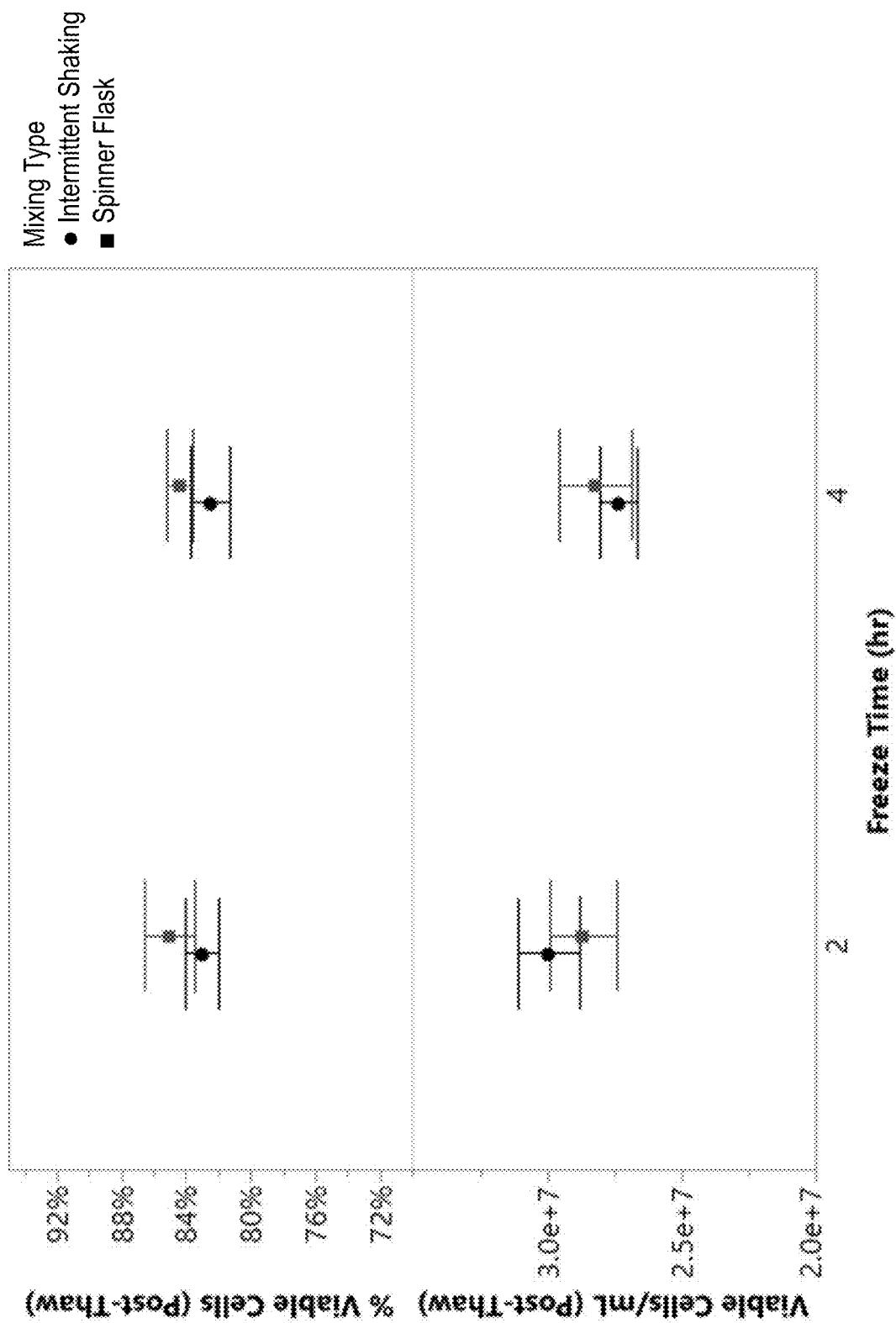
FIG. 8B shows VCD and % viability of post-thawed cells processed by either continuous spinner flask mixing or intermittent shaker flask mixing. Triplets of samples were tested.

The thawed samples were subjected to a two-hour room temperature hold before the VCD and % viability were determined to account for the estimated process time that may be required in the clinic before the thawed drug product are ready to be administered to patients. The data in FIG. 8B show that the VCD and viability of the post-thawed cells were comparable to those of pre-freeze cells under these conditions.

In summary, either continuous mixing in a spinner flask or intermittent shaking in a shaker flask or in a spinner flask allow an extension of the fill to finish time window to at least four hours without affecting VCD or cell viability. The extended fill-finish time window would allow more time to complete filling of large batches of manufactured, formulated engineered immune cells, including CAR T cells, and avoid wastage of unfilled drug product.

What is claimed is:

1. A process of preparing a drug product comprising engineered immune cells, said process comprising the steps of
   (a) formulating engineered immune cells in a composition containing a cryopreservative to form a drug product, wherein the cryopreservative comprises DMSO, and
   (b) filling while mixing in a spinner flask the drug product into one or more containers at room temperature for at least 30 minutes,
   wherein the drug product maintains homogeneity when step (b) is extended to up to about two hours.

2. The process of claim 1, wherein the mixing comprises intermittent mixing or continuous mixing.

3. The process of claim 1, wherein the step of filling while mixing in a spinner flask takes between about two and about four hours, between about two and about five hours, between about two and about six hours, between about three and about six hours, or between about four and six about hours.

4. The process of claim 1, wherein the mixing is intermittent mixing.

5. The process of claim 4, wherein the intermittent mixing comprises mixing for about 1 to about 3 minutes, about every 10 to about every 40 minutes.

6. The process of claim 1, wherein the mixing comprises continuous mixing.

7. The process of claim 1, wherein the mixing is at a speed of about 30 to about 85 rpm.

8. The process of claim 1, wherein the cryopreservative comprises about 3% DMSO to about 10% DMSO.

9. The process of claim 8, wherein the cryopreservative comprises about 5% DMSO.

10. The process of claim 1, wherein the composition further comprises an excipient that enhances viscosity.

11. The process of claim 1, wherein the engineered immune cells are T cells, inflammatory T-lymphocytes, cytotoxic T-lymphocytes, regulatory T-lymphocytes, helper T-lymphocytes, effector T lymphocytes, tumor infiltrating lymphocytes (TILs), NK cells, NK-T-cells, TCR-expressing cells, TCR knockout T cells, dendritic cells, macrophages, killer dendritic cells, mast cells, or B-cells.

12. The process of claim 1, wherein the engineered immune cells are T cells comprising a polynucleotide that encodes a chimeric antigen receptor (CAR T cells).

13. The process of claim 12, wherein the engineered immune cells are allogeneic CAR T cells.

14. The process of claim 12, wherein the engineered immune cells are autologous CAR T cells.

15. The process of claim 1, wherein the engineered immune cells are human cells.

16. A drug product comprising engineered immune cells prepared by the process of claim 1.

17. A method of treating a subject in need thereof comprising administering to the subject the drug product of claim 16.

18. The process of claim 1, wherein the drug product maintains homogeneity when step (b) is extended to up to about three hours.

19. The process of claim 1, wherein the drug product maintains homogeneity when step (b) is extended to up to about three hours, about four hours, about five hours, or about six hours.

20. A process of preparing a drug product comprising engineered immune cells, said process comprising the steps of
   (a) formulating engineered immune cells in a composition containing a cryopreservative to form a drug product, wherein the cryopreservative comprises DMSO, and
   (b) filling while mixing in a spinner flask the drug product into one or more containers at room temperature for at least 30 minutes, wherein the drug product maintains homogeneity when step (b) is extended to up to about two hours, up to about three hours, up to about four hours, up to about five hours, or up to about six hours.

* * * * *